United States Patent
Stothers et al.

(10) Patent No.: US 8,260,389 B2
(45) Date of Patent: Sep. 4, 2012

(54) BLADDER FUNCTION MONITORING METHODS, APPARATUSES, MEDIA AND SIGNALS

(75) Inventors: Lynn Stothers, Vancouver (CA); Roy E. Gagnon, Surrey (CA); Andrew J. MacNab, Vancouver (CA)

(73) Assignee: Hegln (Dalian) Pharmaceuticals, Inc., Dalian, Liaoning Province (CN)

(*) Notice: Subject to any disclaimer, the term of this patent is extended or adjusted under 35 U.S.C. 154(b) by 1783 days.

(21) Appl. No.: 11/404,376

(22) Filed: Apr. 13, 2006

(65) Prior Publication Data

US 2006/0281992 A1 Dec. 14, 2006

Related U.S. Application Data

(63) Continuation-in-part of application No. 10/543,445, filed as application No. PCT/CA2004/001825 on Oct. 15, 2004.

(60) Provisional application No. 60/511,095, filed on Oct. 15, 2003, provisional application No. 60/585,587, filed on Jul. 7, 2004.

(51) Int. Cl.
*A61B 5/1455* (2006.01)

(52) U.S. Cl. ........................... 600/322; 600/310

(58) Field of Classification Search ........... 600/309–344
See application file for complete search history.

(56) References Cited

U.S. PATENT DOCUMENTS

| | | | |
|---|---|---|---|
| 3,814,081 A | 6/1974 | Mori | |
| 4,223,680 A | 9/1980 | Jobsis | |
| 4,281,645 A | 8/1981 | Jobsis | |
| 4,510,938 A | 4/1985 | Jobsis | |
| 4,782,819 A | 11/1988 | Adair | |
| 4,907,876 A | 3/1990 | Suzuki | |
| 5,221,255 A | 6/1993 | Mahurkar et al. | |
| 5,433,216 A | 7/1995 | Sugrue et al. | |
| 5,476,434 A | 12/1995 | Kalb et al. | |
| 5,728,092 A | 3/1998 | Doiron et al. | |
| 5,769,791 A | 6/1998 | Benaron et al. | |
| 5,788,647 A * | 8/1998 | Eggers | 600/526 |
| 5,807,261 A | 9/1998 | Benaron et al. | |
| 5,853,005 A | 12/1998 | Scanlon | |
| 5,916,153 A | 6/1999 | Rhea, Jr. | |

(Continued)

FOREIGN PATENT DOCUMENTS

EP 1187585 A2 4/2006

(Continued)

OTHER PUBLICATIONS

Gagnon RE, Macnab AJ, et al. "Comparison of two spatially resolved NIRS oxygenation indices", J Clin Monit Comput. (2002), 17(7-8):385-91.

(Continued)

*Primary Examiner* — Eric Winakur
*Assistant Examiner* — Marjan Fardanesh
(74) *Attorney, Agent, or Firm* — Richard A. Johnson; Borden Ladner Gervais LLP

(57) ABSTRACT

Bladder function monitoring methods, apparatuses, media and signals are disclosed. A method includes receiving signals from an electromagnetic radiation detector, the signals representing electromagnetic radiation detected from the bladder during irradiance of the bladder with electromagnetic radiation, and further includes storing data indicative of bladder function, in response to the signals. The received signals may represent near infrared (NIR) detected from the bladder during NIR irradiance of the bladder.

28 Claims, 13 Drawing Sheets

U.S. PATENT DOCUMENTS

| | | | |
|---|---|---|---|
| 6,010,453 A | 1/2000 | Fiddian-Green |
| 6,334,064 B1 | 12/2001 | Fiddian-Green |
| 6,406,431 B1 | 6/2002 | Barnard et al. |
| 6,447,462 B1 | 9/2002 | Wallace et al. |
| 6,505,074 B2 | 1/2003 | Boveja et al. |
| 6,519,487 B1 | 2/2003 | Parker |
| 6,690,958 B1 | 2/2004 | Walker et al. |
| 6,699,175 B2 | 3/2004 | Miller |
| 2002/0016536 A1 | 2/2002 | Benni |
| 2002/0080368 A1 | 6/2002 | Ohishi et al. |
| 2003/0084906 A1 | 5/2003 | Roe |
| 2004/0186468 A1 | 9/2004 | Edwards |
| 2006/0281992 A1 | 12/2006 | Stothers et al. |

FOREIGN PATENT DOCUMENTS

| | | |
|---|---|---|
| WO | 02066031 | 8/2002 |

OTHER PUBLICATIONS

Gagnon RE, Macnab AJ, LeBlanc JG. Patterns of change in cytochrome c oxidase redox status, Spectroscopy (2004), 18:161-6.

Gagnon RE, Macnab AJ. "C/C++ Coding for matrix pseudo inverses in clinical near infrared spectroscopy", Comput Methods Biomech Biomed Engin (1998), 1(2):69-86.

Gagnon, R. E., Gagnon, F. A., Macnab A. J. "Comparison of 13 published cytochrome c oxidase near-infrared spectroscopy algorithms", Eur J Appl Physiol Occup Physiol, (1996), 74(6):487-95.

Gagnon, Roy. "Non-Cerebral Applications of NIRS". PowerPoint Presentation given at Heart & Stroke Meeting London, Ontario, Jul. 7, 2003.

Gandjbakhche AH, Nossal R, Bonner RF. "Resolution limits for optical transillumination of abnormalities deeply embedded in tissues", Med Phys (1994), 21(2):185-91.

Garry, D.J, et al. "Emerging roles for myoglobin in the heart", Trends Cardiovasc Med (2003) 13(3):111-6.

Griffiths DE, Wharton DC. "Studies on the electron transport system. XXXV. Purification and properties of cytochrome oxidase", J Biol Chem (1961), 236: 1850-6.

Hayashida M, Kin N, et al. "Cerebral ischaemia during cardiac surgery in children detected by combined monitoring of BIS and near-infrared spectroscopy", Br J Anaesth (2004), 92(5): 662-9.

Heesakkers JP, Vriesema JLj. "The role of urodynamics in the treatment of lower urinary tract symptoms in women", Curr Opin Urol (2005), 15(4):215-21.

Hock C, Villringer K, et al. "Near infrared spectroscopy in the diagnosis of Alzheimer's disease", Ann N Y Acad Sci (1996), 777: 22-9.

Hoffman BM, Roberts JE, et al. "Copper electron-nuclear double resonance of cytochrome c oxidase", Proc Natl Acad Sci USA (1980), 77(3):1452-6.

Homma Y, Kondo Y, et al. "Reproducibility of cystometry in overactive detrusor", Eur Urol (2000), 38(6):681-5.

Hoofd, L., et al. "A modeling investigation to the possible role of myoglobin in human muscle in near infrared spectroscopy (NIRS) measurements", Adv Exp Med Biol (2003) 530:637-43.

Horecker BL. "The absorption spectra of hemoglogin and its derivatives in the visible and near infra-red regions", J Biol Chem (1943), 148:173-183.

Iwasaki K, Nomoto Y, et al. "Vital capacity induction with 8% sevoflurane and N2o causes cerebral hyperemia", J Anesth (2003), 17(1):3-7.

Jobsis F. F. "Noninvasive infrared monitoring of cerebral and myocardial oxygen sufficiency and circulatory parameters", Science (1977), 198(4323):1264-7.

Jones RN. 1985. Analytical applications of vibrational spectroscopy, a historical review. Chemical, Biological, and Industrial Applications of Infrared Spectroscopy. J.R. During, editor. New York, John Wiley and Sons. 1-43.

Kageyama, S., et al. "Clinical experience of simultaneous fiber-urethrocystoscopy and cystometry recording" Nippon Hinyokika Gakkai Zasshi (1993) 84(6):1099-102.

Mills, D.A., et al. "Where is 'outside' in cytochrome c oxidase and how and when do protons get there?", Biochim Biophys Acta (2000) 1458(1):180-7.

Mitchell P. "Coupling of photophosphorylation to electron and hydrogen transfer by a chemiosmotic type of mechanism", Nature (1961), 191:144-8.

Nagdyman N, Fleck T, et al. "Comparison between cerebral tissue oxygenation index measured by near-infrared spectroscopy and venous jugular bulb saturation in children", Intensive Care Med (2005), 31(6):846-50.

NIRO 300 Product Catalogue from Hamamatsu Photonics K.K. Systems Division.

NIRO News Hamamatsu. No. 1, Sep. 1999.

NIRO News Hamamatsu No. 2 Mar. 2000.

Noriyuki T, Ohdan H, et al. "Near-infrared spectroscopic method for assessing the tissue oxygenation state of living lung", Am J Respir Crit Care Med (1997), 156(5): 1656-61.

Ntziachristos V, Chance B. "Accuracy limits in the determination of absolute optical properties using time-resolved NIR spectroscopy", Med Phys (2001), 28(6):1115-24.

Nygaard, I.E., Heit, M. "Stress urinary incontinence", Obstet Gynecol (2004) 104(3):607-20.

Ohdan H, Mizunuma K, et al. "Intraoperative near-infrared spectroscopy for evaluating hepatic venous outflow in living-donor right lobe liver", Transplantation (2003), 76(5): 791-7.

Okada, E., et al. "The effect of overlying tissue on the spatial sensitivity profile of near-infrared spectroscopy", Phys Med Biol (1995) 40(12):2093-108.

Okamoto T, Kanazawa H, et al. "Evaluation of oxygen uptake kinetics and oxygen kinetics of peripheral skeletal muscle during recovery from exercise in patients with chronic obstructive pulmonary disease", Clin Physiol Funct Imaging (2003), 23(5):257-62.

Olesberg, J.T., "Online measurement of urea concentration in spent dialysate during hemodialysis", Clin Chem (2004) 50(1):175-81.

Oster, G., Wang, H. "Reverse engineering a protein: the mechanochemistry of ATP synthase", Biochim Biophys Acta (2000), 1458(2-3):482-510.

Owen-Reece H, Elwell CE, et al. "Use of near infrared spectroscopy to estimate cerebral blood flow in conscious and anaesthetized adult subjects", Br J Anaesth (1996), 76(1):43-8.

Plugge, W., et al. "Near-infrared spectroscopy as an alternative to assess compliance of ampicillin trihydrate with compendial specifications", J Pharm Biomed Anal (1993) 11(6):435-42.

Pogue, B.W., et al. "Characterization of hemoglobin, water, and NIR scattering in breast tissue: analysis of intersubject variability and menstrual cycle changes", J Biomed Opt (2004) 9(3):541-52.

Pringle J, Roberts C, et al. "Near infrared spectroscopy in large animals: optical pathlength and influence of hair covering and epidermal pigmentation", Vet J. (1999), 158(1):48-52.

Puyana JC, Soller BR, et al. "Continuous measurement of gut pH with near-infrared spectroscopy during hemorrhagic shock", J Trauma (1999), 46(1):9-15.

Notification of Reason for Refusal (w/English Translation) dated Aug. 16, 2010 for Japanese Application No. 2006-534553. (2010). 11 pp.

Office Action dated May 26, 2011, issued from the corresponding U.S. Appl. No. 10/543,445.

Kershen RT et al., "Blood flow, pressure and compliance in the male human bladder", Jul. 2002, Journal of urology, 168(1), 121-125.

Abrams, P., et al. "The standardisation of terminology of lower urinary tract function: report from the standardisation sub-committee of the international continence society", Neurology and Urodynamics (2002) 21:167-178.

Abrams, P., et al. "The standardisation of terminology of lower urinary tract function: report from the standardisation sub-committee of the international continence society". Am J Obstet Gynecol (2002) 187:116-26.

al-Rawi PG, Smielewslci P, Kirkpatrick PJ. Preliminary evaluation of a prototype spatially resolved spectrometer. Acta Neurochir Suppl (Wien) (1998), 71: 255-7.

Andriambeloson, E., et al. "Chemical regulation of nitric oxide: a role for intracellular myoglobin?", Redox Rep (2002) 7(3): 131-6.

Arunkalaivanan AS, Mahomoud S, Howell M. "Does posture affect cystometric parameters and diagnoses?" Int Urogynecol J Pelvic Floor Dysfunct, (2004), 15(6):422-4.

Attas, E. Michael, et al. "Near-IR spectroscopic imaging for skin hydration: the long and the short of it", Biopolymers 67(2):96-106.
Barkana Y and Belkin M. "Laser eye injuries", Surv Opthal (2000), 44(6):459-478.
Baseman AG, Baseman JG, Zimmer PE, Lemack GE. "Effect of 6F urethral catheterization on urinary flow rates during repeated pressure-flow studies in healthy female volunteers", (2002), Urology 59(6):843-6.
Belardinelli, R. "Monitoring skeletal muscle oxygenation during exercise by near infrared spectroscopy in chronic heart failure", Congest Heart Fail (1999) 5(3):116-119.
Belville, W.D., et al. "Fiberoptic microtransducer pressure technology: urodynamic implications" Neurourol Urodyn (1993) 12(2): 171-8.
Benaron DA, Kurth CD, Steven JM, et al. "Trans-cranial optical path length in infants by near-infrared phase-shift spectroscopy", J Clin Mon (1995), 11(2); 109-17.
Benesch RE, Benesch R, Yung S. "Equations for the spectrophotometric analysis of hemoglobin mixtures", Anal Biochem (1973), 55: 245-8.
Bonoczk P, Panczel G, Nagy Z. "Vinpocetine increases cerebral blood flow and oxygenation in stroke patients: a near infrared spectroscopy and transcranial Doppler study", Eur J Ultrasound (2002), 15(1-2): 85-91.
Brown DW, Hadway J, Lee TY. "Near-infrared spectroscopy measurement of oxygen extraction fraction and cerebral metabolic rate of oxygen in newborn piglets", Pediatr Res (2003), 54(6):861-7.
Burnett AL, Allen RP, et al. "Near infrared spectrophotometry for the diagnosis of vasculogenic erectile dysfunction", Int J Impot Res (2000), 12(5): 247-54.
Chance B, Cooper CE, et al. "Near-infrared spectroscopy and imaging of living systems", Philosophical Transitions of the Royal Society of London, Series B. (1997), 352(1354): 643-761.
Chance B, Cope M, et al. "Phase measurement of light absorption and scatter in human tissue", Rev Sci Instrum (1998), 69(10): 3457-81.
Chen, D., et al. "Removal of major interference sources in aqueous near-infrared spectroscopy techniques", Anal Bioanal Chem (2004) 379(1):143-8.
Cohn SM, Varela JE, et al. Splanchnic perfusion evaluation during hemorrhage and resuscitation with gastric near-infrared spectroscopy, J Trauma (2001), 50(4): 629-34.
Colier WN, Froeling FM, et al. Measurement of the blood supply to the abdominal testis by means of near infrared spectroscopy, Eur Urol (1995), 27(2): 160-6.
Constantini E, Mearini L, et al. Impact of different sized catheters on pressure-flow studies in women with lower urinary tract symptoms, Neurourol Urodyn (2005), 24(2):106-10.
Corlu, A., et al. "Uniqueness and wavelength optimization in continuous-wave multispectral diffuse optical tomography", Opt Lett (2003) 28(23):2339-41.
Cvitkovic-Kuzmic, A., et al. "Ultrasound assessment of detrusor muscle thickness in children with non-neuropathic bladder/sphincter dysfunction", Eur Urol (2002) 41(2):214-8.
De Blasi RA, Quaglia E, et al. "Muscle oxygenation by fast near infrared spectrophotometry (NIRS) in ischemic forearm", Adv Exp Med Biol (1992), 316:163-72.
de Groot B, Zuurbier CJ, van Beek JH. "Dynamics of tissue oxygenation in isolated rabbit heart as measured with near-infrared spectroscopy". Am J Physiol (1999), 276(5 Pt 2): H1616-24.
Dani C, Bertini G, et al. Brain hemodynamic changes in preterm infants after maintenance dose caffeine and aminophylline treatment, Biol Neonate (2000), 78(1):27-32.
Delpy DT, Cope MC, et al. "Cerebral monitoring in newborn infants by magnetic resonance and near infrared spectroscopy". Scand J Clin Lab Invest Suppl (1987), 188:9-17.
De Visscher G, Leunens V, et al. "NIRS mediated CBF assessment: validating the indocyanine green bolus transit detection by comparison with coloured microsphere flowmetry", Adv Exp Med Biol. (2003), 540:37-45.
Duncan A, Meek JH, et al. "Optical pathlength measurements on adult head, calf and forearm and the head of the newborn infant using phase resolved optical spectroscopy", Phys Med Biol (1995) 40:295-304.

Duncan A, Meek JH, et al. "Measurement of cranial optical path length as a function of age using phase resolved near infrared spectroscopy", Pediatr Res (1996) 39(5):889-94.
Dziki, W., et al. "The use of near-infrared spectroscopy to monitor the mobility of water within the sarafloxacin crystal lattice", J Pharm Biomed Anal (2000) 22(5):829-48.
Edwards AD, Wyatt JS, et al. "Cotside measurement of cerebral blood flow in ill newborn infants by near infrared spectroscopy", Lancet (1988), 2(8614):770-1.
Erdem E, Akbay E, et al. "How reliable are bladder perceptions during cystometry?", Neurourol Urodyn (2004), 23(4):306-9.
Faris, F., et al. "Non-invasive in vivo near-infrared optical measurement of the penetration depth in the neonatal head", Clin Phys Physiol Meas (1991) 12(4)353-8.
Feng, W., et al. "Influence of overlying tissue and probe geometry on the sensitivity of a near-infrared tissue oximeter", Physiol Meas (2001) 22(1):201-8.
Ferrari M, Wei Q, et al. "Time-resolved spectroscopy of the human forearm", Photochem Photobiol (1992), 16:141-53.
Karpefors M, Adelroth P, et al. "Proton uptake controls electron transfer in cytochrome co oxidase", Proc Natl Acad Sci USA (1998), 95:13606-11.
Keller E, Nadler A, et al. "Noninvasive measurement of regional cerebral blood flow and regional cerebral blood volume by near-infrared spectroscopy and indocyanine green dye dilution", Neuroimage (2003), 20(2):828-39. (Erratum in: Neuroimage. Jul. 2004, 22(3):1428).
Kelly CE, Krane RJ. "Current concepts and controversies in urodynamics", Curr Urol Rep (2000), 1(3):217-26.
Kemp GJ, Crowe AV, et al. "Abnormal mitochondrial function and muscle wasting, but normal contractile efficiency, in haemodialysed patients studied non-invasively in vivo", Nephrol Dial Transplant (2004), 19(6):1520-7.
Kety SS, Schmidt CF. "The nitrous oxide method for the quantitative determination of cerebral blood flow in man: theory, procedure, and normal values", J Clin Invest (1948), 27:476-483.
Khan T, Soller B, Naghavi M, Casscells W. "Tissue pH determination for the detection of metabolically active, inflamed vulnerable plaques using near-infrared spectroscopy: an in-vitro feasibility study", Cardiology (2005), 103(1):10-16.
Kim JG, Xia M, Liu H. "Extinction coefficients of hemoglobin for near-infrared spectroscopy of tissue", IEEE Eng Med Biol Mag (2005), 24(2):118-21.
Kim MB, Ward DS, et al. "Estimation of jugular venous $O_2$ saturation from cerebral oximetry or arterial $O_2$ saturation during isocapnic hypoxia", J Clin Monit Comput (2000), 16(3):191-9.
Kinder, M.V., et al. "A non-invasive method for bladder electromyography in humans". Archives of Physiology and Biochemistry (1998) 106(1):2-11.
Kitajima T, Okuda Y, et al. "Response of cerebral oxygen metabolism in the head-up position during laparoscopic cholecystectomy". Surg Laparosc Endosc (1998), 8(6):449-52.
Klaessens JH, Thijssen JM, et al. "Experimental verification of conditions for near infrared spectroscopy (NIRS)" Technol Health Care (2003), 11(1):53-60.
Kohl M, Nolte C, et al. "Determination of the wavelength dependence of the differential pathlength factor from near-infrared pulse signals". Phys Med Biol (1998), 43(6):1771-82.
Kohlhauser C, Bernert G, et al. "Effects of endotracheal suctioning in high-frequency oscillatory and conventionally ventilated low birth weight neonates on cerebral hemodynamics observed by near infrared spectroscopy (NIRS)". Pediatr Pulmonol (2000), 29(4):270-5.
Kraan, J., et al. "Contribution of the haldane effect to the increase in arterial carbon dioxide tension in hypoxaemic subjects treated with oxygen", Adv Exp Med Biol (1985), 191:543-51.
Kragh M, Quistorff B, Lund EL, Kristjansen PE. "Quantitative estimates of vascularity in solid tumors by non-invasive near-infrared spectroscopy". Neoplasia (2001), 3(4):324-30.
Kupriyanov VV, Nigbswander-Rempel S, Xiang B. "Mapping regional oxygenation and flow in pig hearts in vivo using near-infrared spectroscopic imaging". J Mol Cell Cardiol (2004), 37(5):947-57.

Kurth, C.D., et al. "A multiwavelength frequency-domain near-infrared cerebral oximeter", Phys Med Biol (1999) 44(3):727-40.

LeBlanc JG, Blackstock D, et al. 2000. "Effects of propofol on cerebral oxygenation during cardiopulmonary bypass in children", Can J Anaesth (2000), 47(11):1082-9.

Lehr HP, Wickramasinghe Y. "New prototype NIRS instrument [corrected] to investigate multi-regional cerebral blood and tissue oxygenation and haemodynamics". Med Biol Eng Comput (2000), 38(3): 281-6. (Erratum in: Med Biol Eng Comput 2000; 38(4):476).

Lemack GE. "Urodynamic assessment of patients with stress incontinence: how effective are urethral pressure profilometry and abdominal leak point pressures at case selection and predicting outcome?", Curr Opin Urol (2004), 14(6):307-11.

Litscher G, Schwarz G, et al. "Effects of acupuncture on the oxygenation of cerebral tissue", Neurol Res (1998), 20 Suppl 1: S28-32.

MacIntosh BJ, Klassen LM, Menon RS. "Transient hemodynamics during a breath hold challenge in a two part functional imaging study with simultaneous near-infrared spectroscopy in adult humans", Neuroimage (2003), 20(2):1246-52.

Macnab AJ, Gagnon RE, Gagnon FA. "Near infrared spectroscopy for intraoperative monitoring of the spinal cord", Spine (2002), 27(1):17-20.

Macnab AJ, Gagnon R, et al. "Simultaneous $pO_2$ and HbO2 measurement to determine absolute HbO2 concentration for in vivo near infrared spectroscopy", Spectroscopy (2003), 17:289-295.

Maiman TH. "Stimulated Optical Radiation in Ruby", Nature (1960),187(4736):493-4.

Mancini, D.M., et al. "Validation of near-infrared spectroscopy in humans", J Appl Physiol (1994) 77(6):2740-7.

Marshall WJ. "Comparative hazard evaluation of near-infrared diode lasers", Health Phys (1994), 66(5):532-539.

Matcher, S.J., et al. "Use of the water absorption spectrum to quantify tissue chromophore concentration changes in near-infrared spectroscopy", Phy Med Biol (1994) 39(1):177-96.

McBride, T.O.,"Multispectral near-infrared tomography: a case study in compensating for water and lipid content in hemoglobin imaging of the breast", J Biomed Opt (2002) 7(1):72-9.

McGill, S.M., et al. "Lumbar erector spinae oxygenation during prolonged contractions: implications for prolonged work", Ergonomics (2000) 43(4):486-93.

McMurdo ME, Davey PG, et al. "A cost-effectiveness study of the management of intractable urinary incontinence by urinary catheterisation or incontinence pads", J Epidemiol Community Health (1992), 46(3):222-6.

Michel H. "The mechanism of proton pumping by cytochrome c oxidase", Proc Natl Acad Sci USA (1998), 95: 12819-24.

Mehagnoul-Schipper DJ, van der Kallen BF, et al. "Simultaneous measurements of cerebral oxygenation changes during brain activation by near-infrared spectroscopy and functional magnetic resonance imaging in healthy young and elderly subjects", Hum Brain Mapp (2002), 16(1):14-23.

Mikhel'son VA, Prokop'ev GG, Lazarev VV. "Effects of ketamine and propofol on oxygen status and blood content of the brain in children", [Article in Russian] Anesteziol Reanimatol (2001), 1:4-8.

Qiu, Yang, et al. "Identification of myoglobin in human smooth muscle", J Biol Chem (1998) 273(36):23426-23432.

Quaresima V, Sacco S, et al. "Noninvasive measurement of cerebral hemoglobin oxygen saturation using two near infrared spectroscopy approaches", J Biomed Opt (2000), 5(2):201-5.

Raj A, Bertolone SJ, et al. "Assessment of cerebral tissue oxygenation in patients with sickle cell disease: effect of transfusion therapy", J Pediatr Hematol Oncol (2004), 26(5):279-83.

Roll C, Knief J, et al. "Effect of surfactant administration on cerebral haemodynamics and oxygenation in premature infants—a near infrared spectroscopy study", Neuropediatrics (2000), 31(1):16-23.

Rostrup E, Law I, et al. "Cerebral hemodynamics measured with simultaneous PET and near-infrared spectroscopy in humans", Brain Res (2002), 954(2):183-93.

Saraste, Matthias, "Oxidative phosphorylation at the fin de siecle", Science (1999) 283:1488-1493.

Sassaroli A, Fantini S. "Comment on the modified Beer-Lambert law for scattering media", Phys Med Biol (2004), 49(14):N255-7.

Sato H, Kiguchi M, et al. 2004. "Practicality of wavelength selection to improve signal-to-noise ratio in near-infrared spectroscopy", Neuroimage (2004), 21(4):1554-62.

Sato K, Shirane R, et al. "Effect of inhalational anesthesia on cerebral circulation in Moyamoya disease", J Neurosurg Anesthesiol (1999), 11(1): 25-30.

Schmidt, W.D., et al. "Contact-free spectroscopy of leg ulcers: principle, technique, and calculation of spectroscopic wound scores", J Invest Dermatol (2001) 116(4):531-5.

Shah, N., et al. "Spatial variations in optical and physiological properties of healthy breast tissue", J Biomed Opt (2004) 9(3):534-40.

Shaw C, Williams K, et al. "Patient satisfaction with urodynamics: a qualitative study", J Adv Nurs (2000), 32(6):1356-63.

Shimizu N, Gilder F, et al. "Brain tissue oxygenation index measured by near infrared spatially resolved spectroscopy agreed with jugular bulb oxygen saturation in normal pediatric brain: a pilot study", Childs Nerv Syst (2005), 21(3):181-4.

Siderias J, Guadio F, Singer AJ. "Comparison of topical anesthetics and lubricants prior to urethral catheterization in males: a randomized controlled trial", Acad Emerg Med (2004), 11(6):703-6.

Smith, K.C.: The Science of Photobiology: new topics in photobiology, Chapter 15, K.C. Smith, editor. New York, Plenum Press. p. 400-9, 1977.

Sokol DK, Markand ON, et al. "Near infrared spectroscopy (NIRS) distinguishes seizure types", Seizure (2000), 9(5): 323-7.

Srinivasan, S., et al. "Interpreting hemoglobin and water concentration, oxygen saturation, and scattering measured in vivo by near-infrared breast tomography", Proc Natl Acad Sci USA (2003) 100(21):12349-54.

Steinberg F, Rohrbom HJ, et al. "NIR reflection measurements of hemoglobin and cytochrome aa3 in healthy tissue and tumors. Correlations to oxygen consumption: preclinical and clinical data", Adv Exp Med Biol (1997), 428:69-27.

Sugano N, Inoue Y, et al. "Evaluation of buttock claudication with hypogastric artery stump pressure measurement and near infrared spectroscopy after abdominal aortic aneurysm repair". Eur J Vasc Endovasc Surg (2003), 26(1):45-51.

Sullivan J, Lewis P, et al. "Quality control in urodynamics: a review of urodynamic traces from one centre", BJU Int (2003), 91(3):201-7.

Suto T, Fukuda M, et al. "Multichannel near-infrared spectroscopy in depression and schizophrenia: cognitive brain activation study", Biol Psychiatry (2004), 55(5): 501-11.

Suzuki S, Takasaki S, et al. "A tissue oxygenation monitor using NIR spatially resolved spectroscopy", Proc SPIE (1999), 3597: 582-92.

Svendsen LB, Flink P, et al . "Muscle oxygen saturation during surgery in the lithotomy position", Clin Physiol (1997), 17(5): 433-8.

Takac S, Stojanovic S. "Classification of laser irradiation and safety measures", Med Pregl (1998), 51(9-10): 415-418.

Tanabe P, Steinmann R, Anderson J, Johnson D, Metcalf S, RingHum E. "Factors affecting pain scores during female urethral catheterization", Acad Emerg Med (2004), 11(6):699-702.

Thach AB. "Laser injuries of the eye". Int Opthahmol Clin (1999), 39(2):13-27.

Thiruchelvan, N., et al. "Bladder wall tension during physiological voiding and in patients with an unstable detrusor or bladder outlet obstruction", BJU Int (2004) 93(7):1117-8.

Torricelli A, Quaresima V, Pifferi A, Biscotti G, Spinelli L, Taroni P, Ferrari M, Cubeddu R. "Mapping of calf muscle oxygenation and haemoglobin content during dynamic plantar flexion exercise by multi-channel time-resolved near-infrared spectroscopy". Phys Med Biol (2004), 49(5):685-99.

Tsukihara T, Aoyama H, et al. "Structures of metal sites of oxidized bovine heart cytochrome c oxidase at 2.8 angstrom", Science (1995), 269:1069-74.

Tu T, Chen Y, et al. "Analysis on performance and optimization of frequency-domain near-infrared instruments", J Biomed Opt (2002), 7(4):643-9.

Van Bel F, Shadid M, et al. "Effect of allopurinol on postasphyxial free radical formation, cerebral hemodynamics, and electrical brain activity", Pediatrics (1998), 101(2): 185-93.

Van de Hulst HC. Light scattering by small particles. New York, Dover Publications, 1957, p. 28-129.

van der Zee P, Cope M, et al. "Experimentally measured optical path lengths for the adult head, calf and forearm and the head of the newborn infant as a function of interoptode spacing", Adv Exp Med & Biol (1992), 316:143-53.

Varotsis C, Zhang Y, et al. Resolution of the reaction sequence during the reduction of $O_2$ by cytochrome oxidase Proc Natl Acad Sci USA (1993), 90: 237-41.

Verkhovsky MI, Morgan JE, Wikström M. "Intramolecular electron transfer in cytochrome c oxidase: a cascade of equilibria", Biochemistry (1992), 47:11860-3.

Vogel AI. A text-book of quantitative inorganic analysis including elementary instrumental analysis. $3^{rd}$ Edition. London, Longmans Green & Co., 1961, p. 740-2.

Wang TL, Hung CR. "Role of tissue oxygen saturation monitoring in diagnosing necrotizing fasciitis of the lower limbs", Ann Emerg Med (2004), 44(3):222-8.

Weiss, Markus, et al. "Transcutaneously measured near-infrared spectroscopic liver tissue oxygenation does not correlate with hepatic venous oxygenation in children", Canadian Journal of Anesthesia (2002), 49(8):824-829.

Wikström M, Bogachev A, et al. "Mechanism of proton translocation by the respiratory oxidases. The histidine cycle", Biochim Biophys Acta (1994), 1187(2):106-11.

Wikström M. "Mechanism of proton translocation by cytochrome c oxidase: a new four-stroke histidine cycle", Biochim Biophys Acta (2000), 1458:188-98.

Wyatt JS, M Cope, et al. "Measurement of optical path length for cerebral near infrared spectroscopy in newborn infants", Dev Neurosci (1990), 12:140-4.

Yamamoto K, Komiyama T, et al. "Contralateral stenosis as a risk factor for carotid endarterectomy measured by near infrared spectroscopy", Int Angiol (2004), 23(4):388-93.

Yamashita Y, Maki A, Koizumi H. "Wavelength dependence of the precision of noninvasive optical measurement of oxy-, deoxy-, and total-hemoglobin concentration", Med Phys (2001), 28(6):1108-14.

Yang, J.M., et al. "Bladder wall thickness on untrasonographic cystourethrography: affecting factors and their implications", J Ultrasound Med (2003) 22(8):777-82.

Yoshitani K, Kawaguchi M, et al. "Comparison of changes in jugular venous bulb oxygen saturation and cerebral oxygen saturation during variations of haemoglobin concentration under propofol and sevoflurane anaesthesia". Br J Anaesth (2005), 94(3):341-6.

Yoshiya I, Shimada Y, Tanaka K. "Spectrophotometric monitoring of arterial oxygen saturation in the fingertip", Med Biol Eng Comput (1980), 18:27-32.

Zaslaysky D, Gennis RB. 2000. Proton pumping by cytochrome oxidase: progress, problems, and postulates. Biochim Biophys Acta 1458:164-79.

Zhang, A.P., et al. "Mode recoupling in a novel Bragg grating pair", Opt Lett (2003) 28(7):519-21.

Zhou, G.X., et al. "Determination and differentiation of surface and bound water in drug substances by near infrared spectroscopy", J Phar Sci (2003) 92 5):1058-65.

Mourant et al. "Diagnosis of Tissue Pathology with Elastic Scattering Spectroscopy," Conference Proceedings vol. 1 IEEE Laser and Electro-Optics Society 1994,, $7^{th}$ Annual Meeting Oct. 31-Nov. 3, 1994, Boston, MA pp. 17-18.

* cited by examiner

BLADDER FUNCTION MONITORING METHODS, APPARATUSES, MEDIA AND SIGNALS

CROSS-REFERENCE TO RELATED APPLICATIONS

This application is a continuation-in-part of U.S. patent application Ser. No. 10/543,445 filed Jul. 25, 2005, which is a U.S. national stage of PCT International Patent Application No. PCT/CA2004/001825 filed Oct. 15, 2004, which claims the benefit of priority from: U.S. Patent Application No. 60/511,095 filed Oct. 15, 2003, U.S. Patent Application No. 60/585,587 filed Jul. 7, 2004 and Canadian Patent Application No. 2,473,192 filed Jul. 7, 2004. This application is also a continuation-in-part of the aforementioned PCT International Patent Application No. PCT/CA2004/001825 filed Oct. 15, 2004, which claims the benefit of priority from: U.S. Patent Application No. 60/511,095 filed Oct. 15, 2003, U.S. Patent Application No. 60/585,587 filed Jul. 7, 2004 and Canadian Patent Application No. 2,473,192 filed Jul. 7, 2004.

BACKGROUND OF THE INVENTION

1. Field of Invention

The present invention relates to urology, and more particularly, to methods, apparatuses, media and signals for monitoring bladder function in an animal.

2. Description of Related Art

Voiding dysfunction affects over 50% of the population. A primary tool used to understand how the bladder functions is to test bladder urodynamics. Urodynamics can measure bladder volume, whether the bladder has normal sensation during filling and whether the bladder contracts with appropriate strength when a patient/subject voids. Urodynamics testing can also inform us if a patient has an obstruction to the bladder or, if there is leakage of urine (incontinence—involuntary leakage), then what type of leakage it is. Urodynamics are done to diagnose a variety of underlying problems of the bladder. It is also used following implementation of treatment strategies to demonstrate success or failure. A traditional urodynamic test consists of three components—the non invasive uroflow (which gives information about bladder emptying), the Cystometrogram (which gives information about bladder filling) and the pressure flow study (which gives additional information about bladder emptying).

To perform standard urodynamics, the patient is asked to attend with a full bladder. The patient is asked to void onto a scale, which produces a tracing of how quickly they can void, and the total voided volume. Then, two catheters are positioned, one in bladder and one in the rectum. From this point onwards the test is invasive in nature. Furthermore, the presence of the catheter in the urethra is a known confounding factor because the catheter itself can cause obstruction to voiding, can be irritating to the bladder causing false contractions, and/or can have side effects including bleeding and infection.

It is also useful for urologists to have a direct measurement of how strong the bladder muscle itself contracts. To do so, a catheter is placed into the rectum and it is connected to a pressure transducer that measures abdominal pressure. A second catheter is placed into the centre of the bladder via the urethra and is also connected to a pressure transducer. It is known that the pressure in the centre of the bladder is a reflection of the abdominal pressure plus the pressure generated by the bladder muscle itself. Therefore, it is possible to calculate the pressure generated by the bladder muscle indirectly. However, conventional urodynamics testing does not provide a direct measure of bladder muscle activities. This deficit is apparent when the flow of urine is measured without the use of catheters. The volume of urine voided onto a scale provides a tracing of how quickly the volume of urine is voided. This is called the 'non invasive uroflow'. However, with uroflow testing no information is recorded from the bladder muscle. Both a weak bladder muscle and an obstructed bladder with high pressure in the bladder muscle wall can produce a dribbling type of urinary stream with reduced flow rates.

SUMMARY OF THE INVENTION

Illustrative embodiments of the present invention may provide non-invasive ways of measuring bladder function or urodynamics. Such non-invasive techniques may be performed in conjunction with traditional invasive and/or non-invasive urodynamics testing, if desired.

In accordance with one illustrative embodiment of the invention, there is provided a method of monitoring bladder function in an animal having a bladder. The method includes receiving signals from an electromagnetic radiation detector, the signals representing electromagnetic radiation detected from the bladder during irradiance of the bladder with electromagnetic radiation. The method further includes storing data indicative of bladder function, in response to the signals.

Receiving may include receiving signals representing near infrared (NIR) detected from the bladder during NIR irradiance of the bladder.

The method may further include irradiating the bladder with an electromagnetic radiation emitter while detecting the electromagnetic radiation from the bladder.

Irradiating and detecting may include irradiating and detecting during bladder activity.

Irradiating and detecting may respectively include emitting and detecting near infrared (NIR), and storing may include storing near infrared spectroscopy (NIRS) data.

The method may further include positioning the emitter and the detector on the animal's skin adjacent to the animal's bladder.

Irradiating may include emitting coherent electromagnetic radiation.

Positioning may include ultrasonic positioning.

Positioning the detector on the animal's skin may include positioning the detector about 10 mm cephalic of the symphysis pubis of an adult human.

Ultrasonic positioning may include transmitting ultrasonic energy from a transducer, and receiving reflected ultrasonic energy to determine the location of the animal's bladder.

Emitting NIR may include emitting electromagnetic radiation within a wavelength range of 750-950 nanometers.

The stored NIRS data may be indicative of the animal's level of one or more of: oxygenated hemoglobin ($HbO_2$); de-oxygenated hemoglobin (Hb); oxidized cytochrome a, $a_3$; reduced cytochrome a, $a_3$; oxidized minus reduced forms of the cytochrome C oxidase (Cyt).

The method may further include shielding the emitter and the detector from ambient electromagnetic radiation.

The method may further include attenuating the electromagnetic radiation with which the bladder is irradiated. Attenuating may include filtering the electromagnetic radiation with which the bladder is irradiated. Filtering may include filtering the electromagnetic radiation with a filter chamber having selectable variable density filters, operable to incrementally filter emitted electromagnetic radiation.

The method may further include obtaining ultrasonic measurements of bladder parameters of the animal.

Positioning may include positioning the emitter and the detector to have a separation of about 15-90 mm therebetween.

Receiving may include receiving signals representing detected near infrared electromagnetic radiation (NIR) from the bladder, and storing may include storing near infrared spectroscopy (NIRS) data for the animal. The NIRS data may correspond to a first plurality of times during a first time period.

The method may further include receiving and storing urodynamic data for the animal, the urodynamic data corresponding to a second plurality of times during a second time period. The first and second pluralities of times may be recorded with reference to a common timeline.

The method may further include receiving and storing subject feedback data for bladder sensation corresponding to an additional plurality of times during an additional time period. The animal may be a human subject.

The method may further include comparing the NIRS data with one or more of the urodynamic data and subject feedback data in association with the common timeline. For example, the method may include comparing the NIRS data with the urodynamic data in association with the common timeline.

The method may further include displaying a representation of the NIRS data. For example, the method may include displaying the NIRS data with one or more of the urodynamic data and subject feedback data in association with the common timeline. Thus, the method may include displaying a representation of the NIRS data with a representation of the urodynamic data in association with the common timeline.

The urodynamic data may include one or more of the following: bladder volume data; void volume data; uroflow data; filling cystometrogram data; and pressure flow data.

The NIRS data may be indicative of the animal's level of one or more of: oxygenated hemoglobin ($HbO_2$); de-oxygenated hemoglobin (Hb); oxidized cytochrome a, $a_3$; reduced cytochrome a, $a_3$; and oxidized minus reduced forms of the cytochrome C oxidase (Cyt).

The first plurality of times may be different from the second plurality of times. Alternatively, the first plurality of times may be the same as the second plurality of times. In either case, the first time period may at least partly overlap with the second time period.

Similarly, the first plurality of times may be different from the additional plurality of times, or alternatively, may be the same as the additional plurality of times. The first time period may at least partly overlap with the additional time period.

In accordance with another illustrative embodiment of the invention, there is provided an apparatus for monitoring bladder function in an animal having a bladder. The apparatus includes means for receiving signals from an electromagnetic radiation detector, the signals representing electromagnetic radiation detected from the bladder during irradiance of the bladder with electromagnetic radiation. The apparatus further includes means for storing data indicative of bladder function, in response to the signals.

The apparatus may further include means for performing the various functions described herein.

In accordance with another illustrative embodiment of the invention, there is provided an apparatus for monitoring bladder function in an animal having a bladder. The apparatus includes a storage medium, and a processor circuit in communication with an electromagnetic radiation detector and with the storage medium. The processor circuit is programmed or otherwise configured to receive signals from the detector, the signals representing electromagnetic radiation detected from the bladder during irradiance of the bladder with electromagnetic radiation. The processor circuit is further configured to store data indicative of bladder function in the storage medium, in response to the signals.

The processor circuit may be further configured to co-operate with various devices such as those described herein, to implement or facilitate the implementation of the various methods described herein.

In accordance with another illustrative embodiment of the invention, there is provided a computer-readable medium storing instruction codes for directing a processor circuit to receive signals from an electromagnetic radiation detector, the signals representing electromagnetic radiation detected from the bladder during irradiance of the bladder with electromagnetic radiation. The instruction codes further direct the processor circuit to store data indicative of bladder function, in response to the signals.

In accordance with another illustrative embodiment of the invention, there is provided a signal embodied in a communications medium, the signal including code segments for directing a processor circuit to receive signals from an electromagnetic radiation detector, the signals representing electromagnetic radiation detected from the bladder during irradiance of the bladder with electromagnetic radiation. The signal further includes code segments for directing the processor circuit to store data indicative of bladder function, in response to the signals.

Such codes on a medium, or code segments in a signal, may include codes for directing the processor circuit to co-operate with various devices such as those described herein, to implement or facilitate the implementation of the various methods described herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
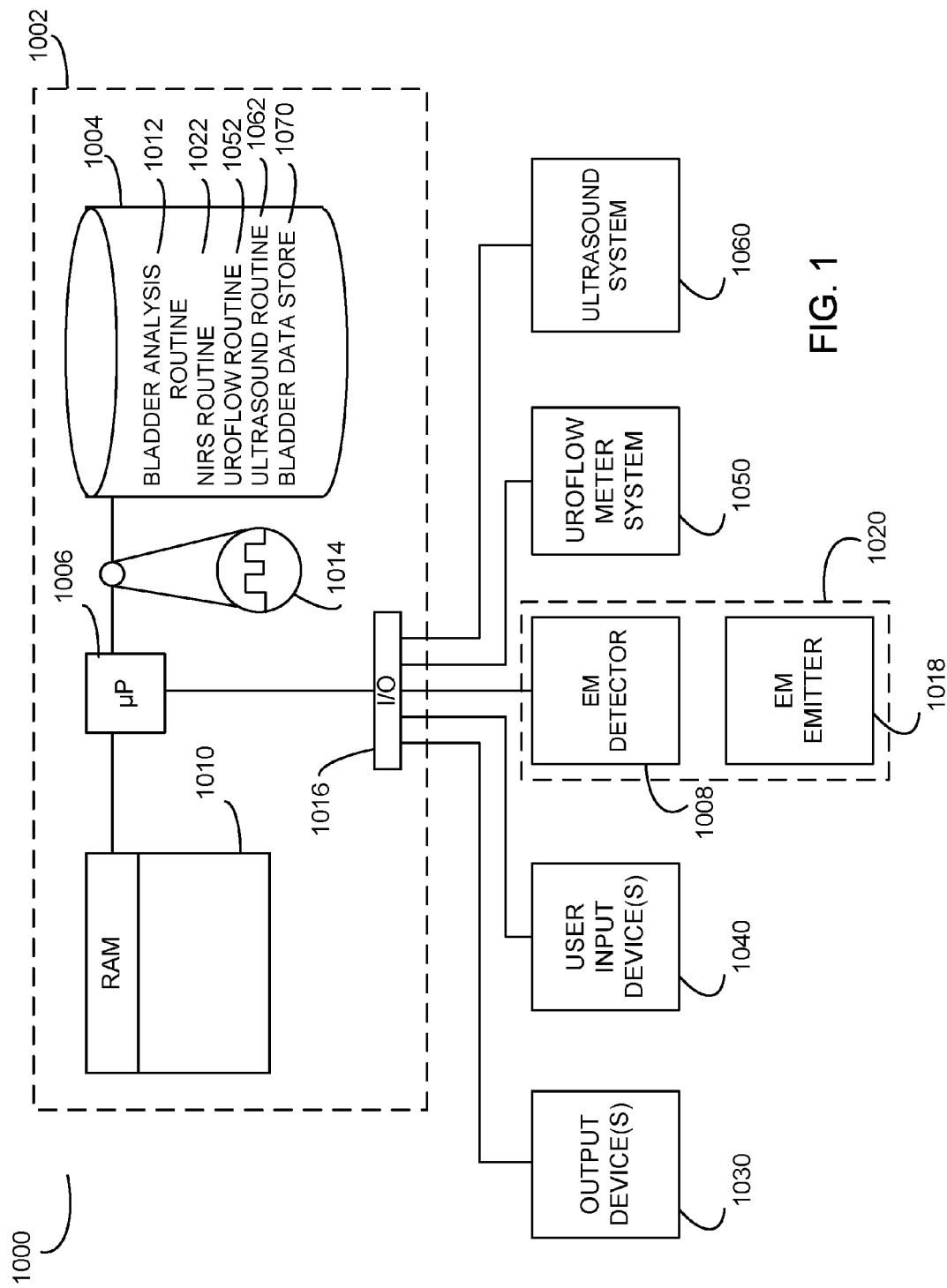
FIG. 1 is a block diagram of a system for monitoring bladder function, according to a first embodiment of the invention.

Referring to FIG. 1, a system for monitoring bladder function in an animal having a bladder (not shown) according to a first embodiment of the invention is shown generally at 1000. In this embodiment, the system 1000 includes an apparatus 1002 for monitoring bladder function. More particularly, in this embodiment the apparatus 1002 includes a storage medium 1004, and a processor circuit 1006 in communication with an electromagnetic radiation detector 1008 and with the storage medium 1004.

In this embodiment, the processor circuit 1006 is configured to receive signals from the detector 1008, the signals representing electromagnetic radiation detected from the bladder during irradiance of the bladder with electromagnetic radiation. In this embodiment, the processor circuit 1006 is further configured to store data indicative of bladder function in the storage medium 1004, in response to the signals.

More particularly, in this embodiment the apparatus 1002 includes a computer, and the processor circuit 1006 includes a microprocessor. More generally, in this specification, including the claims, the term "processor circuit" is intended to broadly encompass any type of device or combination of devices capable of performing the functions described herein, including (without limitation) other types of microprocessors, microcontrollers, other integrated circuits, other types of circuits or combinations of circuits, logic gates or gate arrays, or programmable devices of any sort, for example, either alone or in combination with other such devices located at the same location or remotely from each other, for example. Additional types of processor circuits will be apparent to those ordinarily skilled in the art upon review of this specification, and substitution of any such other types of processor circuits is considered not to depart from the scope of the present invention as defined by the claims appended hereto.

In this embodiment, the processor circuit 1006 is in further communication with a memory device 1010, which in the present embodiment includes a random access memory (RAM).

In the present embodiment, the storage medium 1004 includes a hard disk drive. Alternatively, however, any other suitable storage device, such as a compact disc (CD), other types of magnetic disks or diskettes, optical storage devices, magnetic tapes, random access memories (RAMs), programmable read-only memories such as EPROMs, EEPROMs or FLASH memories, for example, or any other type of memory or storage device, either at the location of the processor circuit or located remotely therefrom, may be substituted if desired.

In this embodiment, the storage medium 1004 acts as a computer-readable medium storing instruction codes, including a bladder analysis routine 1012, for directing the processor circuit 1006 to cause the various methods described herein to be carried out. Thus, in this embodiment the storage medium 1004 acts as a computer-readable medium storing instruction codes for directing the processor circuit 1006 to receive signals from the electromagnetic radiation detector 1008 representing detected electromagnetic radiation from the bladder while the bladder is being irradiated with electromagnetic radiation, and for directing the processor circuit 1006 to store data indicative of bladder function, in response to the signals. It will be appreciated that the bladder analysis routine 1012 and other instruction codes stored in the storage medium 1004 are communicated to the processor circuit 1006 via electrical signals, such as that shown at 1014, for example. Alternatively, such instruction codes or code segments thereof may be supplied to the processor circuit 1006 via similar signals from other devices, located in proximity to or remotely from the processor circuit 1006.

In this embodiment, the bladder analysis routine 1012 configures the processor circuit 1006 to define, in the storage medium 1004, a bladder data store 1070, for storing the various types of data indicative of bladder function as described herein.

In this embodiment, the processor circuit 1006 is in communication with the electromagnetic radiation detector 1008 via an input/output (I/O) interface 1016, through which the processor circuit 1006 is also in communication with an electromagnetic radiation emitter 1018.

More particularly, in this embodiment the electromagnetic radiation detector 1008 and emitter 1018 are components of an electromagnetic radiation measurement system 1020. More particularly still, in this embodiment the electromagnetic radiation measurement system 1020 includes a NIRO-300™ near infrared spectrophotometer, manufactured by Hamamatsu Photonics. Thus, in this embodiment the electromagnetic radiation detector 1008 includes a near infrared detector, and the electromagnetic radiation emitter includes a near infrared emitter. Alternatively, other suitable types of electromagnetic radiation detectors and emitters may be substituted.

In this embodiment, the storage medium 1004 also stores a NIRS routine 1022. In this embodiment, the NIRS routine 1022 configures the processor circuit 1006 to receive NIRS data from the electromagnetic radiation measurement system 1020, and to permit a user to graph or save the resulting data. More particularly, in this embodiment the NIRS routine 1022 includes software available from Hamamatsu Photonics, for use in conjunction with the NIRO-300 near infrared spectrophotometer.

In this embodiment, the processor circuit 1006 is in further communication, via the I/O interface 1016, with one or more output devices 1030, and one or more user input devices 1040. More particularly, in this embodiment the output devices 1030 include a display monitor and a printer, and the user input devices 1040 include a keyboard, a mouse and a remote toggle switch. Alternatively, other suitable input and output devices or combinations thereof may be substituted as desired for a given application.

In this embodiment, the processor circuit 1006 is in further communication, via the I/O 1016, with a uroflow meter system 1050. More particularly, in this embodiment the uroflow meter system includes a collection chamber into which a patient or subject empties its bladder. In this embodiment, the storage medium 1004 also stores a uroflow routine 1052, which configures the processor circuit 1006 to receive signals from the uroflow meter system 1050, and to evaluate uroflow parameters such as ejection flow rate and momentary voided volume therefrom.

In this embodiment, the processor circuit 1006 is in further communication, via the I/O 1016, with an ultrasound system 1060. More particularly, in this embodiment, the ultrasound system 1060 is used to provide an indication of the volume of urine within the bladder, both before and after urination, to determine the amount of residual urine in the bladder that could not be voided. In this embodiment, the storage medium 1004 also stores an ultrasound routine 1062, which configures the processor circuit 1006 to receive signals from the ultrasound system 1060 indicative of such measurements.

Illustrative Methods and Apparatus
Urodynamics
 Urodynamics may be performed using the Laborie urodynamics equipment. Urodynamics typically involves 3 sub-components.
A. Uroflow
 The patient arrives to the lab with a full bladder. The non-invasive uroflow is done in the standing position for male patients and in the sitting position for female patients. The patient spontaneously voids to empty as much as possible from their bladder. A catheter is then inserted in the bladder and the remaining urine drained and its volume measured.
B. Filling Cystometrogram (CMG)
 An 8 Fr double lumen urodynamic catheter, a urodynamic rectal balloon catheter and EMG perineal leads are placed in the standard fashion. The patient is supine. Sterile, room temperature water is infused at rates consistent with the subject's bladder condition using a Laborie pump. Patients are asked to indicate "first sensation", sensation of "urgency", and "capacity" in keeping with the definitions of the International Continence Society.
 "First sensation" or "first desire, to void" is defined as a normal desire to void and is described as the feeling that leads the subject to pass urine at the next convenient moment, but voiding can be delayed if necessary. A strong desire to void is defined as a persistent desire to void without the fear of leakage. Whereas, "urgency" is defined as a strong desire to void accompanied by fear of leakage or fear of pain. The term "capacity" must be qualified. Maximum cystometric capacity, in patients with normal sensation, is the volume at which the subject feels that they can no longer delay micturition. In the absence of sensation the maximum cystometric capacity cannot be defined in the same terms and is the volume at which the clinician decides to terminate filling. In the presence of sphincter incompetence the maximum cystometric capacity may be significantly increased by occlusion of the urethra e.g. by Foley catheter. The "functional bladder capacity", or voided volume is more relevant and is assessed from a frequency/volume chart (urinary diary). The "maximum (anaesthetic) bladder capacity" is the volume measured after filling during a deep general or spinal/epidural anaesthetic, specifying fluid temperature, filling pressure and filling time.
 At capacity, the bladder is emptied by syringe via the catheter, and the patient is changed to the sitting position using the electronic urodynamics table/chair. Bladder filling is repeated, at the same infusion rate, again recording indicators of bladder sensation, but at maximum capacity, the patient is asked to spontaneously void. (This is the beginning of the pressure flow segment of the study.) Not all labs do the filling Cystometrogram in two positions (supine and upright). However, it can be done for completeness because it is known that a change in the patient position during bladder filling can unmask certain pathologic problems.
C. Pressure Flow
 With the urethral catheter, rectal balloon and EMG leads in place, the patient is asked to void spontaneously into the flow meter. This produces a pressure flow tracing. The Abrams-Griffiths nomograms are used when plotting the pressure flow study to indicate zones of obstructed flow and non-obstructed flow. On a standard urodynamic tracing a detrusor pressure (pdet) value is a reflection of the pressure in the bladder caused by the bladder muscle and is calculated by subtracting abdominal pressure (pabd) from vesical pressure (pves). Pves is the pressure that is measured inside the bladder, with a catheter that was specifically designed for pressure monitoring in the urinary tract. The pressure information obtained is a combination of the pressure being exerted on the bladder by the abdominal contents, the weight or pressure of any urine in the bladder and the force that the detrusor muscle is exerting on that fluid. The Resting pressure usually refers to the pressure in an empty bladder and may change with position. A normal bladder resting pressures may vary between 8 and 40 cmH2O, depending upon the particular patient and position during study. Pabd is measured by placing a special catheter either in the rectum or the vagina. Abdominal pressure information is significant because the bladder is contained in the floor of the abdominal cavity and it is important to isolate pressures and activities occurring in the bladder itself. The detrusor pressure is a subtracted pressure that is calculated by subtracting the pabd from the pves. A pressure flow tracing displays a waveform that represents the actual activities taking place in the bladder during the CMG. Abdominal straining, gas and the weight of the abdominal contents may produce artifacts, which can be removed from the information being processed from the catheter in the bladder.

Near Infrared Spectroscopy (NIRS)

A. Illustrative NIRS Urodynamic Method

Examples of suitable NIRS instruments are commercially available from Hamamatsu Photonics KK (325-6 Sunayama-Cho, Hamamatsu-City, 430-8587 Japan). In this embodiment, it will be recalled that the electromagnetic radiation measurement system 1020 includes a NIRO-300™ near infrared spectrophotometer from Hamamatsu Photonics. The present inventors have found that the NIRO-300™ has data collection intervals suitable for urodynamic analysis and is capable of measuring cytochrome c oxidase, an important component of NIRS in urology applications.

Emitters for NIRS may for example be selected from filtered white light, direct-gap gallium aluminum arsenide (GaAlAs) semiconductor lasers, and/or light emitting diodes (i.e. iRED). The white light source can be either a Xenon or Halogen bulb and its filter component usually consists of a segmented spinning disk comprised of a specific filtering wavelength in each segment. The advantage of a white light source is that a great number wavelengths can be accommodated. GaAlAs lasers are specific to the infrared emission region and can be set to unique wavelengths by adjusting the gap width—they are pulsed to allow various wavelengths to be sequentially synchronized. Lasers have the advantage of having sufficient power output to achieve significant tissue depth penetration. iRED's are comprised of positive and negative semiconductor materials directly in contact with each other with the materials and interface junction selected to achieve one specific wavelength. iRED's have the advantages of low input power requirement, high efficiency with minimal heat generation, and long operational lifetime. If a variety of different infrared emissions are desired, a single light source, or alternatively a plurality of light sources, such as a series of separate lasers, for example, may be used. "Light" as used herein refers to electromagnetic radiation in general, and is not limited to "visible" light. Thus, the term "light" as used herein may include electromagnetic radiation at wavelengths that are not visible to the human eye, notably including NIR wavelengths, for example. Coherence as used in relation to "light" (i.e. coherent light) is a unique property of laser light and arises from the stimulated emission process to provide the amplification. A common stimulus triggers the emission events, which provide the amplified light resulting in emitted photons, which are "in step" and have a definite phase relation to each other. Coherence is described in terms of temporal coherence and spatial coherence.

The NIRO-300™ near infrared spectrophotometer emits sequentially gated nanosecond pulses of four wavelengths of near infrared light-photons in the 760 to 920 nanometer range. It detects the loss of light intensity when the emitted photons are absorbed by changes in the concentration of oxygenated hemoglobin ($HbO_2$), and de-oxygenated hemoglobin (Hb), as well as by changes in the net difference of the oxidized minus reduced forms of the cytochrome C oxidase also known as the copper moiety of mitochondrion cytochrome a, $a_3$ (Cyt). Furthermore, NIRS can detect oxygenated myoglobin ($MbO_2$); and de-oxygenated myoglobin (Mb). However, in the 760 to 920 nm range Mb & MbO2 spectra are indistinguishable from Hb & $HbO_2$. The hemoglobin data provides insight regarding delivery of oxygen to the tissues and the cytochrome data indicates whether the tissues utilized the delivered oxygen. In the urology setting, the primary design requirement is to collect and report data at rates faster than one-second intervals. This is desirable because of the high rates of change that can occur during filling and voiding of the bladder.

NIRS optodes, consisting of an NIRS emitter and NIRS detector, can be positioned externally over the bladder. NIRS optodes placement may have the NIRS emitter adjacent NIRS detector along any of the coronal, sagittal, transverse or diagonal planes, or posterior or anterior, left or right, caudal or cephalic, or arbitrary relative to any of the planes. NIRS optode placement may alternatively have the NIRS emitter opposite from the NIRS detector. For example, one optode may be placed on the anterior and the other on the posterior of the animal, or one may be placed on the left while the other is placed on the right. Generally, the orientation of the emitter and detector can be horizontal (left to right), vertical (caudal to cephalic), or arbitrary and would depend on the anatomical structure and age of the animal/subject to be monitored. The localization of optodes will generally benefit from proximity to the subject's bladder. The present apparatus and methods may be applied to any animal having a bladder.

NIRS optode (NIRS emitter and NIRS detector) placement and orientation can be established relative to the physical location of the bladder as for example generally being about 10 mm cephalic of the symphysis pubis in the midline of an adult human, or by ultrasound detection of the bladder or other detection methods known in the art.

The separation of NIRS emitter and NIRS detector, where the arrangement is "adjacent", would generally be about 15-90 mm, from center to center. Alternatively, the separation may be between 25-80 mm, or 35-70 mm or 40-60 mm or 35-55 mm. However, separation may be adjusted depending on laser power being used. For example reliable NIRS data can be collected with separations of about 35-55 mm if a 1 mW laser power is used. Generally, if laser power is increased then a greater separation is desirable because there will be greater depth of penetration and consequently, a wider base of return by refracted photons. However, increased laser power may be hazardous to tissue. Similarly, less laser power would yield narrower separations but at shallower depth of penetration. However, if the laser power is too low the light will not penetrate sufficiently beyond skin thickness to interrogate the bladder.

Pulse duration and frequency are technical constraints and NIRS typically uses multiple wavelengths of light to mathematically solve for multiple chromophores (i.e. X number of equations for X number of unknowns). Although lasers can be built to emit discrete wavelengths, photon detectors typically detect all light regardless of wavelength. Consequently, NIRS engineering uses pulsed lasers so that the bursts arriving at the detectors can be timed to be associated with the timed sequence of pulses from the various lasers (one laser per wavelength, as one laser per chromophore). The laser pulse duration and frequency of pulsing, as a combination, should have sufficient "off" phase to not have an overlap between emissions and also have sufficient "on" phase to permit the photons to traverse to the detector. As the number of lasers is increased there is greater risk of mistiming. Fortunately, the speed of light as fast as it is, pulse duration/frequency are generally easily matched so that there is little risk of overlap even if a hundred lasers are used rather then only the 4 as used by the NIRO-300™. Generally, there is little need to modify pulse duration or frequency. Monitoring resolution generally increases with number of lasers. Rather than having 3 lasers for 3 chromophores (i.e. Hb, $HbO_2$, & Cyt) the NIRO-300™ uses 4 lasers, the one redundancy providing better resolution.

Thus, in a particular embodiment, depending upon the type of NIRS illumination detectors and associated equipment (e.g. filters) employed, and the surrounding environment in which NIRS is conducted, the NIRS illumination detectors may not be able to distinguish between input NIRS emissions and the ambient background light from any other sources of natural or artificial light that may be present. Therefore, in such embodiments, it may be beneficial to shield the emission and detection surfaces of the subject's skin against ambient lighting. Positioning of the light shield, NIRS emitter and NIRS detector as mentioned above, may be accomplished ultrasonically, whereby a subject's bladder is located using an ultrasound probe.

Furthermore, ultrasound may also be employed by the ultrasound system 1060 to provide an indication of the volume of urine within the bladder. Ultrasound volume readings before and after urination are made to determine the amount of residual urine in the bladder that could not be voided. Ultrasound is the preferred method of measurement because it can be done non-invasively on the skin surface rather than via catheterization.

Once positioned, the light shield may be secured with an adhesive tape. Alternative attachment means may be selected from a urologic diaper, an adjustable belt, an adjustable strap system, an adhesive glue, static electrical charge, vacuum suction and weighted tab system or other systems known in the art. The attachment means chosen is likely to depend on the duration of time data is to be collected and type of data collection (i.e. clinical setting or home monitoring).

For home monitoring or long term monitoring in a care facility the NIRS apparatus may be made portable so that a subject is able to wear the apparatus or carry the apparatus for extended periods of time to monitor bladder filling and voiding. The optodes and light shield may be held in position with a belt and the laser(s), power source, control unit and data recording equipment worn in a backpack.

NIRS data collection may be initiated prior to uroflow and may be continued throughout the entire study for each patient. The initiation of the NIRS prior to the start of the uroflow is advantageous. Current urodynamic methods generally allow for data collection to begin only from the time the urine hits the scale. With the NIRS, data may be recorded about the bladder contraction, which occurs prior to voiding. Event markers may be simultaneously placed in the NIRS and the Laborie data streams during the CMG to indicate starting the infusion, bladder sensation, bladder capacity and any change in position by the patient.

A patient undergoing NIRS monitoring in a urodynamic clinic may be asked to arrive from home with a suitably full bladder, which they then empty during the monitoring. Alternatively, a catheter can be passed into the bladder via the urethra and used to infuse sterile saline while NIRS monitors the bladder filling. In this embodiment, the procedure for NIRS monitoring begins with the patient lying on a cot while a portable ultrasound fluid volume meter is passed over their abdomen to identify the location of the bladder. The NIRS adhesive light shield incorporating illumination and detection probes is adhered to the skin surface in the region identified by the ultrasound apparatus. The NIRS device is then calibrated to account for background field intensity, skin colour, and tissue density via an iterative process that may involve addition of optical attenuation neutral density filters to account for the patient's unique physical parameters (i.e. body mass, skin pigmentation, skin thickness, bladder size, detruser thickness, prior pelvic surgery, obesity, suprapubic fat pad, tissue water content). Following calibration, the patient lies supine for an arbitrary number of minutes sufficient to establish that a stable pre-voiding baseline monitoring level has been achieved. Given a stable baseline, NIRS monitoring continues at 1 to 10 Hz intervals while the patient proceeds to empty the bladder into the uroflow meter system 1050, or more particularly, into a collection chamber thereof known by urologists as a uroflow meter, which may be designed into the cot or a standalone uroflow meter.

In this embodiment, the collection chamber of the uroflow meter system 1050 is digitally interfaced to the processor circuit 1006. In the present embodiment, the uroflow routine 1052 configures the processor circuit 1006 to evaluate uroflow parameters, such as ejection flow rate and momentary voided volume, in response to signals received from the uroflow meter system. 1050. These parameters from the uroflow meter are typically done standing or sitting by males, and sitting by females. Alternatively, the same NIRS oxygenation monitoring and non-NIRS urine ejection/volume monitoring can be performed with the patient seated on a portable commode. At the start of voiding, the patient says aloud that he/she is commencing to void, and this event is marked into the NIRS data stream by toggling a momentary switch on the NIRS device. Alternatively, this event may be marked by use of one of the user input devices 1040, such as a keyboard, a mouse, a toggle switch, or other type of input device, in communication with the processor circuit 1006. Once the patient perceives the bladder is empty, the patient says so aloud and this event is similarly marked into the NIRS data stream. Following this second event, NIRS monitoring continues for a period of minutes sufficient to confirm that a stable post-voiding baseline level has been established. Alternatively, remote toggling of event markers on the NIRS apparatus may allow the patient to toggle the event marker where a self-determination response needs to be recorded. Patient self-toggling of the event marker is important in urologic examinations because the patient's awareness is a key component of incontinence.

If a desired diagnosis procedure involves monitoring during filling, a standard urodynamic infusion/pressure catheter may be installed in the typical manner without regard for NIRS monitoring. The same NIRS steps as described above for a full bladder may be carried out for an empty bladder being filled via the catheter. Some urology examinations may involve sequential filling and emptying via the catheter, and these can be done in the same NIRS manner as already described. Upon completion of monitoring, the NIRS light shield may be removed from the patient, and the collected data may be transferred to a the processor circuit 1006 under the direction of the bladder analysis routine 1012 and the NIRS routine 1022, for post analysis, display formatting, and interpretation. Alternatively, the collected NIRS data may be communicated to the processor circuit 1006 in real time as it is collected, if desired.

Light Shield Apparatus

Current NIRS ambient light shields are intended for placement on the patient's forehead and are not well suited for positioning over the bladder for urology examinations as described herein. Urologists use ultrasonography to estimate bladder wall thickness, cross sectional area, and retention volume, but this is difficult in conjunction with NIRS because light shields currently available for conventional NIRS applications occlude the ultrasound waves from gaining access to the skin surface. If the ultrasound work precedes application of the NIRS shielding, residues of the ultrasound barrier gel may weaken the adhesive on the NIRS shield. The weakened shield may then peel away from the patient under the weight of the NIRS cabling, resulting in leakage of ambient light which corrupts the NIRS calibration so that the data collection is impaired. Also, handling the NIRS shield to install the emitter and detector along with double faced adhesive tape as an applique to the patient's skin is troublesome and compromises the timely flow of patients through the urology clinic. The present embodiment involves the use of an NIRS light shield, which facilitates simultaneous NIRS and ultrasonography and reduces the likelihood of ambient light leakage. However, light shields without the configuration for ultrasound may also be used where ultrasound probe use is not required. Where no ultrasound is used, a urethral catheter can be used to measure the residual urine.

Generally, NIRS ambient light shields are designed on the principle that the shield should be pliable enough to conform to the curved, hard, surface of the skull, and therefore an adhesive may be used to ensure conformity, and edge sealing, as well as to prevent slippage. Also the shields are intended for use on infants and unconscious patients who may be restless over the long course of brain observations and their tendency to squirm can cause movement artifacts in the data stream with a poorly applied light shield. However, in NIRS urology applications the sampling time is often brief (except with home monitoring), conformity and slippage are not an issue given the soft structure of the abdomen, oversized shields can be devised that encompass the abdomen so that edge sealing is not of concern. The patient can either hold the shield in place by hand pressure, by wearing a urologic diaper incorporating the shield, by a weighted belt, or by having a "wool and hook" adjustable belt constrain the shield. Such alternatives may thereby eliminate the need for, and delay caused by, applying an adhesive.

An illustrative example of a NIRS light shield apparatus may include an opaque shield body made from a disposable foam sheet drape, wherein the opaque shield body incorporates an aperture for ultrasonography and retainers (emitter and detector) or retaining pods for mounting the NIRS emitter and NIRS detector terminals.

Alternatively the opaque light shield may be dimensioned to suit the particular application and the size of the subject, whether an infant, child, teen, or adult. However, a light shield for infants may be designed to drape the entire waist if both anterior and posterior sides are exposed to ambient light, or drape the entire abdomen if the subject lying supine. In adults a light shield of 160 mm by 160 mm may be used, for example, and larger shields may be preferred in some instances. The intensity of ambient light is typically the greatest factor in determining shield size. In a surgical setting where NIRS may be desirable, where there are powerful overhead lamps, it may be desirable to drape the entire region to be monitored rather than rely on the light shield alone. A similar strategy may be desirable for NIRS monitoring in urology where bright sunlight is present or other ambient light is present. An alternative to light shields is to perform monitoring in a dark room.

In this embodiment, the light shield defines an emitter aperture to allow emitted NIR light to emerge from the transmitting fiber optic bundle or NIRS emitter and to enter into the tissue. The light shield also defines a detector aperture to allow reflected photons to emerge from the tissue and strike the surface of a conventional photodiode collection array or NIRS detector. Furthermore, the light shield defines an ultrasound probe aperture, through which an ultrasound probe can be placed to permit orientation of the shield on the skin surface centrally over the detected bladder. The light shield apparatus may also comprise a detector retaining clip or detector retainer, to constrain or hold the photodiode array terminal or NIRS detector on the light shield. The light shields may also have an emitter retaining clip or emitter retainer to constrain or hold the fiber optic bundle emission prism or NIRS emitter. The light shield may also have a flexible, hinged, flap, or alternative ultrasound probe closure to occlude the ultrasound aperture when the ultrasound probe is not present, thereby reducing ambient light contamination. The light shield may also have interface cable retention means, which may take the form of opposing saddle shaped ridges intended to constrain the interface cables leading from the photodiode (NIRS detector) and emission (NIRS emitter) terminals. The light shield and associated components may be made of any light occluding or opaque material such as wood, rubber, metal foil, foam, or rubber impregnated cloth etc. The shield can be held in place by any suitable attachment means, such as (but not limited to) fluid or mechanical means, static electrical charge, ultrasound barrier gel, vacuum suction, adhesive glues or tapes, strapping belts, or weighted tabs, for example.

In operation the light shield apparatus may be removed from sealed packaging, the neck of an ultrasound probe may be placed through the shield's ultrasound probe aperture. The ultrasound probe could then be moved over the lower abdomen to locate and measure the intact bladder. The ultrasound probe could then be kept immobile over the measurement site while the light shield is positioned over the subject's bladder and held in place on the skin surface. After which the ultrasound probe may be removed and set aside. The light shield may then be attached to the skin surface by a variety of attachment means. With the light shield in place, the NIRS detector and NIRS emitter terminals may be attached into their respective retainers or retaining pods on the light shield surface. The ultrasound aperture cover may then be closed and the NIRS analysis could begin, with the calibration/attenuation and subsequent data collection. At any time during the NIRS analysis light detection can be suspended, the light shield's ultrasound probe aperture may be opened, and an ultrasound probe measurement made without disturbing the shield placement. At the completion of data collection, the NIRS emitter and detector (and weight belt, if supine) may be removed from the ambient light shield and the shield may then be removed from the patient and discarded.

As discussed earlier herein, photodiode or NIRS detector and photon counting-tubes of illumination detectors used in some NIRS devices may not be able to distinguish between NIRS emissions and ambient background light from natural or artificial sources. Thus, in such embodiments, it may be desirable to shield the emission and detection surfaces the of the subject's skin and areas on a subject's skin to which the light shield apparatus is applied.

The light shield apparatus may also be useful to position the NIRS emitter at a desired distance from the NIRS detector by virtue of the positioning of the emitter and detector apertures within the opaque light shield body. The separation between the NIRS emitter and NIRS detector may be 15-90 mm, from center to center, for example. Alternatively, the separation may be between 25-80 mm or 35-70 mm or 40-60 mm or 35-55 mm. However, separation may be adjusted depending on laser power being used. For example reliable NIRS data can be collected with separations of 35-55 mm if a 1 mW laser power is used. Generally, if laser power is increased then a greater separation is desirable because there will be greater depth of penetration and consequently, a wider base of return by refracted photons. Similarly, less laser power would generally yield narrower separations with shallower depth of penetration. However, if the laser power is too low the light may not penetrate sufficiently to interrogate the bladder and if the laser power is too high it may be hazardous to the subject's tissues.

Figure 1A:
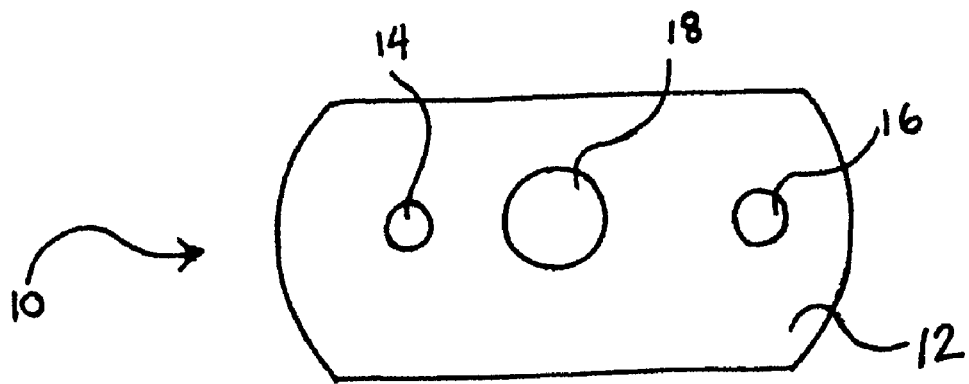
FIG. 1A is a bottom plan view of an embodiment of an illustrative light shield apparatus.
Figure 1B:
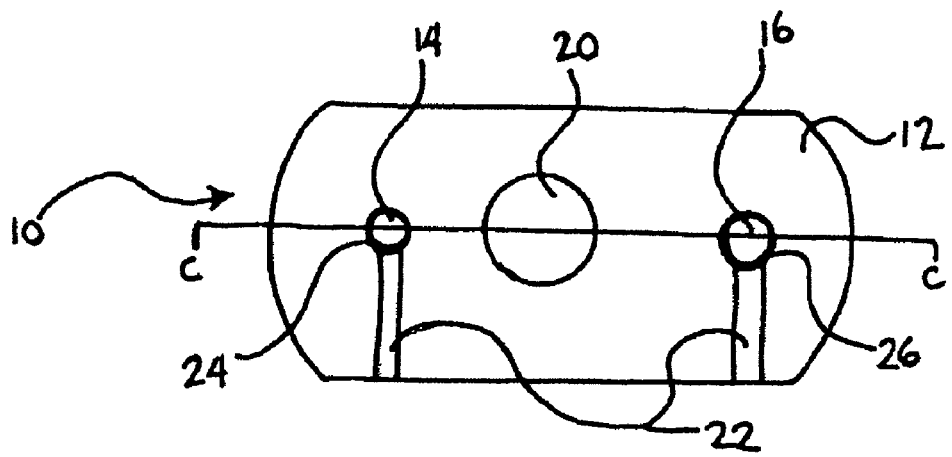
FIG. 1B is a top plan view of the apparatus shown in FIG. 1A.

Referring to FIG. 1A, an illustrative example of a light shield apparatus for use in connection with the present embodiment is shown generally at 10. FIG. 1A shows a view of the light shield apparatus towards the skin interface surface of the apparatus which would be placed on a subject's skin. An opaque body shield is shown at 12, the opaque body shield 12 defines three apertures, an emitter aperture 14, a detector aperture 16 and an ultrasound probe aperture 18. These apertures permit access to defined areas on a subject's skin to which the light shield apparatus may be applied. FIG. 1B is a view of the embodiment towards the surface opposite the skin interface surface shown in FIG. 1A. The light shield apparatus is again shown generally at 10, the opaque shield body is shown at 12, the emitter aperture is shown at 14 and the emitter retainer is shown at 24. The detector aperture is shown at 16 and the detector retainer is shown at 26. Unlike FIG. 1A, FIG. 1B shows an ultrasound probe closure 20 positioned within the ultrasound probe aperture 18 (not shown). FIG. 1B also shows interface cable channels at 22.

Figure 1C:
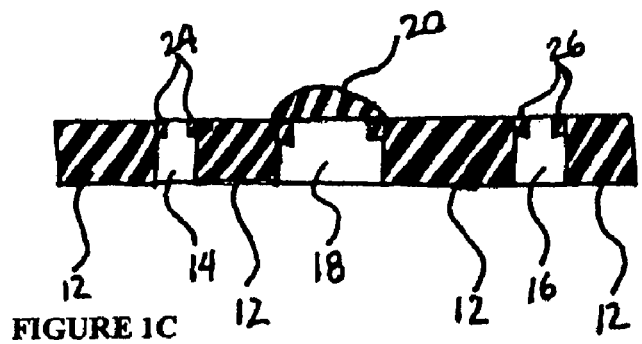
FIG. 1C is a cross sectional side view of the apparatus shown in FIG. 1B as taken through line c.

Referring to FIG. 1C a side cross-section view through the apparatus of FIG. 1B along cross-section line c in FIG. 1B. The opaque shield body is shown at 12 in cross section the emitter aperture defined by the opaque shield body is shown at 14 and the emitter retainer is shown at 24. Similarly, the detector aperture defined by the opaque body is shown at 16 and the detector retainer is shown at 26. Also shown in cross section is the ultrasound probe closure 20 fitted within the ultrasound probe aperture defined by the opaque body 12.

An ultrasound probe (not shown) may be inserted through the ultrasound probe aperture 18 defined by the opaque shield body 12 and used to position the light shield apparatus over a subject's bladder. Once positioned the ultrasound probe may be removed from the light shield apparatus and the light shield may be secured in position. Once in position the ultrasound probe closure 20 may be inserted in the ultrasound probe aperture 18 to reduce ambient light from interference with NIRS measurements. However, the ultrasound probe closure 20 may be removed periodically to allow for ultrasound probing. For example, to determine bladder volume during NIRS monitoring. An emitter (not shown) may be inserted in the emitter aperture 14 defined by the opaque shield body 12 and retained by the emitter retainer 24 to hold the emitter in place relative to the light shield apparatus. Similarly, a detector (not shown) may be positioned within the detector aperture 16 defined by the opaque shield body 12 and held in place by the detector retainer 26. Once the emitter and detector are positioned within the light shield apparatus the emitter may begin emission of NIRS light towards the bladder with subsequent detection by the detector.

Filtering Apparatus

Clinical near infrared spectrophotometers (NIRS) are generally optimized for cerebral tissue oxygenation monitoring and the NIRS output illumination is of sufficient power to send photons through the thickness of intact human skin, skull, and brain cortex, as well as to allow refracted near infrared (NIR) light photons to re-emerge at the skin surface for detection. NIR light refraction occurs by chance encounter of photons against reflective surfaces at unpredictable incident angles. Therefore, photons re-emerging at the skin surface have a broad region of diffusion surrounding the initial point of entry into the tissue. A few re-emerging photons will arrive next to the initial point of entry, and few will arrive very far away from the initial point; however, the majority will arrive at a zone of optimal intensity midway between these extremes. The NIRS photon detector should ideally be placed within the re-emerging photons' zone of optimal intensity. This can be done either by varying the mechanical separation between the fiber optic bundle emitting terminal (NIRS emitter) and photodiode detector array terminal (NIRS detector), or by attenuating the emitted light to a fixed separation of both terminals. During the NIRS calibration phase, a signal ratio between output and input illuminations is evaluated to determine whether the detector placement is optimal.

Given the large surface area available for cerebral NIRS monitoring, either fixed or variable terminal separations can be utilized and adapted to the clinical need.

However, in the case of urodynamic NIRS monitoring, in which the ratio of bladder size to illumination power typically yields an optimal re-emergence zone outside of the bladder's perimeter, the illumination power may advantageously be attenuated to allow a narrower NIRS terminal separation. Attenuation may be achieved in various ways, such as by passing the NIRS emissions through an optical neutral density filter prior to entering the tissues, for example. The degree of attenuation could vary between patients depending upon body mass, skin pigmentation, skin thickness, bladder size, and detruser thickness. To accommodate this variability, diversity in neutral density filters may be preferable to adjusting the NIRS laser illumination power itself, as the latter adjustment may be difficult in a particular embodiment (e.g., the latter adjustment may involve replacing the entire laser series).

Conventionally, optical attenuation is achieved by sequentially threading different filters into a fitting on the NIRS fiber optic bundle. This is a tedious process since it requires an iterative process of elimination to arrive at the correct filtering density. In the present embodiment, to avoid the delays caused by threading, unthreading, and re-threading an indeterminate combination of filters, a set of sliding filter plates is housed in a filter chamber attached to the fiber optic cable leading to the NIRS emitter from a NIRS laser or NIRS laser series.

The filter chamber may have 4 filter plates, wherein each filter plate consists of an opaque carrier plate. The carrier plate may have two perimeter notches, which can act as position alignment stop when engaged by the protrusion of a spring loaded, round tipped, centering rod. The carrier plate may also have an optical neutral density filter, and a clear aperture. An engager push rod or actuator may be connected to the rounded end of the carrier plate nearest the aperture. A spring loaded return rod may be connected to the rounded end of the carrier plate nearest the filter. During use, the engager rod may be pushed against the return rod spring tension to select either the filter or clear aperture as identified by the tactile feel and sound of the centering rod sliding into an alignment notch. Within the chamber, the filter carrier plates may be aligned with light guide channels. The channels can minimize photon leakage within the span caused by the separation between the carrier plates, which in this embodiment is sufficient to allow the user to activate a single carrier plate with one finger. The chamber may have a direct connection to the laser illumination interface at one end of the chamber; and, a threaded connection to a fiber optic bundle (NIRS emitter) at the other end of the chamber.

The filter plates may each contain a step filter and a clear aperture. For example the step filters in a 4 plate system may be set in increments equal to 6% of the total unfiltered output illumination. The first plate has a 6% filter. The second plate has a 12% filter. The third plate has an 18% filter, and the fourth plate has a 24% filter. By selecting filters and clear apertures in combination, 12 progressive steps of attenuation can be achieved ranging from 0% to 72% of the total output illumination. Alternatively, the 4 plate system can be composed of 5% step filters to allow 12 attenuations from 0% to 60%, as well as 4% steps to allow ranges of 0% to 48%. Alternatively, a 3 plate system will allow 8 levels of attenuation ranging from 0% to either 48% in 6% steps, 56% in 7% steps, 64% in 8% steps or 72% in 9% steps.

Automatic attenuation is also possible by replacing the carrier plate engager and return push rods with miniature, threaded worm drive, electric motors interfaced to a software algorithm cycling through all possible combinations of filter steps and halting upon selection of an acceptable level of attenuation. Alternatively, the attenuation apparatus may optionally be positioned on a rotatable dial to select the desired filter setting.

As an alternative to attenuation, multiple lasers could be incorporated into a single apparatus suitable for a range of physical parameters for an animal.

Figure 2A:
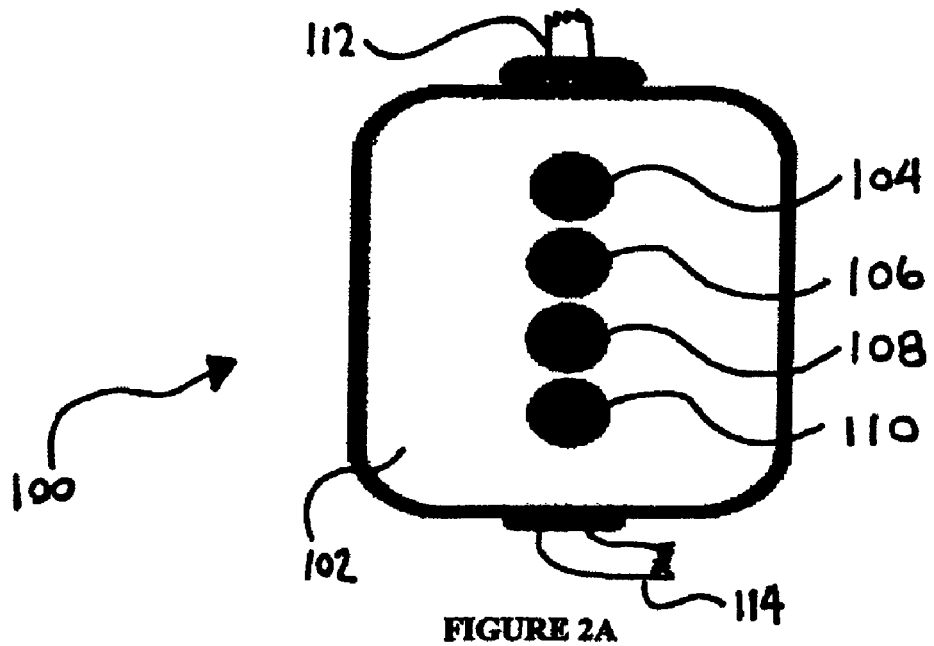
FIG. 2A is a front view of an illustrative filtering apparatus.

Referring to FIG. 2A, an illustrative example of a filter chamber apparatus for use in conjunction with an embodiment of the invention is shown generally at 100. FIG. 2A shows a side view of a filter chamber 102 and selection means 104, 106, 108 and 110. An input light guide 112 is shown entering the filtering chamber 102 and an output light guide is shown exiting at 114.

Figure 2B:
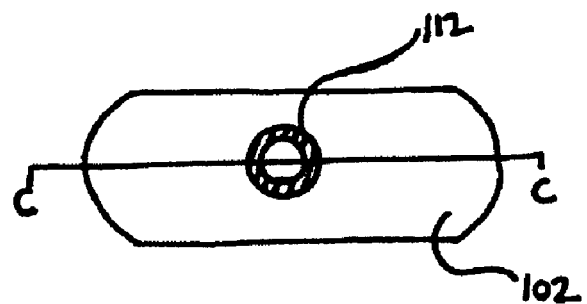
FIG. 2B is a top plan view of the apparatus shown in FIG. 2A.
Figure 2C:
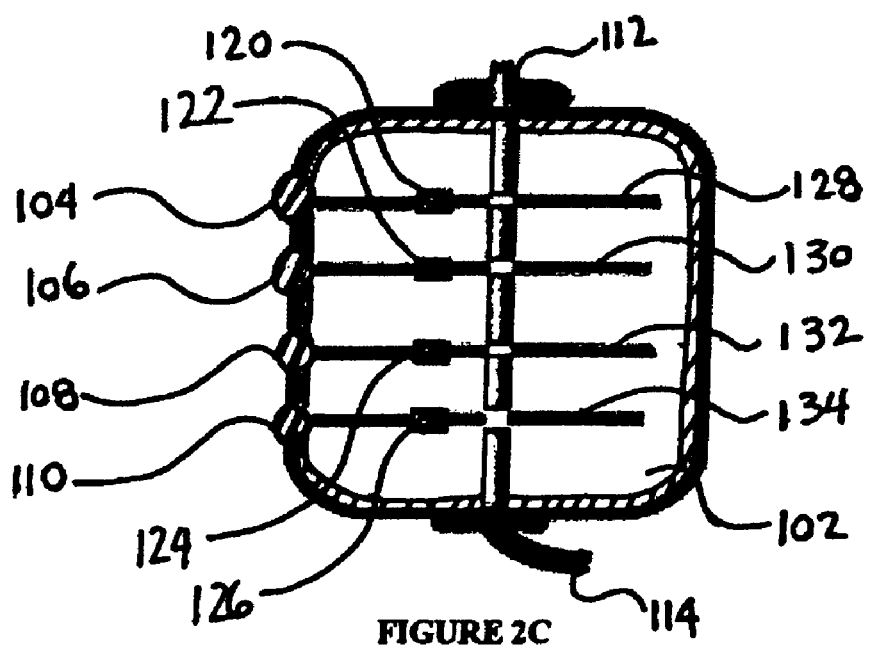
FIG. 2C is a cross sectional side view of the apparatus shown in FIG. 2B as taken through line c.

At FIG. 2B a top view of the filtering apparatus of FIG. 2A is shown. The filter chamber 102 and input light guide 112 are also indicated. Referring to FIG. 2C a cross sectional view of the filtering apparatus is shown with the cross section taken along line c as shown in FIG. 2B. The input light guide 112 and output light guide 114 are shown at opposite ends of the filter chamber 102. The light guide is shown traversing the filter chamber and intersecting with filter actuator rods 128, 130, 132 and 134 each respectively biased against selection means 104, 106, 108 and 110 respectively. Each actuation rod has a filtered and unfiltered position, with the filters shown at 120, 122, 124 and 126 in an unfiltered position.

Light traveling down the light guide from 112 to position 114 passes through the filtering apparatus shown generally at 100 and in particular through the filter chamber 102. Actuator rods (128, 130, 132 and 134) may be actuated by corresponding selection means (104, 106, 108 and 110) to alternatively position a filter (120, 122, 124 and 126) in the path of the light traveling through the light guide from position 112 to position 114 by one or more of the filters mentioned above. Alternatively, one or more of the filters can be disengaged by the same selection means to remove said filters from the path of the transmitted light.

Bladder and Voiding Dysfunction

The present methods for monitoring bladder function (bladder urodynamic monitoring) may be of particular use in the diagnosis of disorders related to bladder and voiding dysfunction. Disorders related to the bladder and voiding dysfunction may have a variety of causes and diagnosis may be confounded by the limitations of current urodynamic testing. Bladder and voiding dysfunction may be the result of one or more structural or physiological abnormalities of the bladder itself or may be indicative of dysfunction elsewhere in the urinary tract (both upper and lower).

Patients having lower urinary tract dysfunction (LUTD) may have dysfunction of their bladder, bladder neck, prostate and urethra, as well as any vessels and the nerve supply to this region. Furthermore, patients with LUTD are likely to exhibit lower urinary tract symptoms (LUTS) as defined by ABRAMS P. et al. (Neurourology and Urodynamics (2002) 21:167-178.). Patients having upper urinary tract dysfunction may have dysfunction in their kidneys and ureters, as well as any vessels and the nerve supply to this region. Upper urinary tract dysfunction may also include the physiological transport of urine from the kidneys to the bladder. Patients having upper urinary tract dysfunction may also exhibit symptoms associated with this region. Bladder function monitoring of a patient may be useful in determining the underlying cause of the upper and lower urinary tract dysfunction in the patient.

Types of voiding dysfunction which may be diagnosed or in which diagnosis may be aided using the NIRS monitoring methods described herein may be selected from any lower urinary tract dysfunction or upper urinary tract dysfunction or selected from the following International Continence Society accepted definitions:

Incontinence: Reduced ability to control urine flow—involuntary passage of urine.

Incontinence due to Pregnancy: Bladder control problems after pregnancy.

Incontinence in children: Reduced ability or inability to control urine flow in children.

Spastic Bladder or Reflex Bladder: Incontinence with urgency or uninhibited detrusor contractions—bladder that is unable to hold the normal amount of urine, or by a bladder that does not empty properly, and thus always retains some urine in it. Another version of this is an irritated or unstable bladder, which may tell the brain that it is necessary to empty the bladder when it is only partly full.

Atonic Bladder or Flaccid Bladder: this condition occurs when the bladder is 'lazy' and fails to empty. Messages of bladder fullness are no longer perceived and the bladder overfills, which leads to stretching and weakness of the bladder muscle. This tends to cause overfill and overflow incontinence, with some frequency, urgency as well as dribbling or hesitancy. There is considerable risk of infection as urine can overflow or be sent back up (reflux) towards the kidneys, which might cause damage in the longer term.

Dyssynergic Bladder (Sphincter Dyssynergia): also known as 'conflicting bladder', as the bladder and sphincter no longer function in conjunction with each other, their actions being uncoordinated. The bladder may contract to empty, but the sphincter also contracts to retain the urine, or both the bladder and sphincter are relaxed. Symptoms include urgency followed by hesitancy, dribbling or incontinence. One of the important problems with dyssynergia is that if the bladder contracts but the sphincter fails to open to allow the bladder to empty, then there may be urine reflux back up towards the kidneys.

Sphincter incompetence: Corticospinal tract interruption will interfere with voluntary interruption of urinary stream (using external sphincter). Sympathetic denervation will interfere with internal sphincter. Incomplete bladder emptying.

Vesical-Sphincter Dyssynergia: Usually have incontinence due to involuntary detrusor contractions. Sometimes external sphincter contracts at same time as bladder, looking like bladder outlet obstruction! (Small voiding volumes, high post-void residual volumes).

(Neurogenic) Areflexia/Hyporeflexia of Detrusor: Detrusor areflexia is a bladder that does not generate contractions. Detrusor hyperreflexia is defined as the presence of involuntary detrusor contractions, usually at low volumes. This can produce symptoms of urgency and urge incontinence.

Urinary retention: bladder-emptying problem. Acute urinary retention is the sudden inability to urinate, causing pain and discomfort. Causes can include an obstruction in the urinary system, stress, or neurologic problems. Chronic urinary retention refers to the persistent presence of urine left in the bladder after incomplete emptying. Common causes of chronic urinary retention are bladder muscle failure, nerve damage, or obstructions in the urinary tract.

Bladder papilloma: Benign tumor in the bladder.

Cystocele: occurs when the wall between a woman's bladder and her vagina weakens and lets the bladder droop into the vagina. This condition may cause discomfort and problems with emptying the bladder. In some women, a fallen bladder stretches the opening into the urethra, causing urine leakage when the woman coughs, sneezes, laughs, or does any action that puts pressure on the bladder. So a bladder that has dropped from its normal position may cause two kinds of problems—unwanted urine leakage and incomplete emptying of the bladder.

Cystitis: Bladder infection or inflammation.

Interstitial Cystitis: is a chronic bladder disorder also known as painful bladder syndrome and frequency-urgency-dysuria syndrome. In this disorder, the bladder wall can become inflamed and irritated. The inflammation can lead to scarring and stiffening of the bladder, decreased bladder capacity, pinpoint bleeding, and, in rare cases, ulcers in the bladder lining.

Autoimmune Interstitial Cystitis: Autoimmune bladder inflammation.

Neurogenic Bladder: Problems with the nerves controlling the bladder and urination. The nerves carry messages from the brain to the muscles of the bladder telling them either to tighten or release. In a neurogenic bladder, the nerves that are supposed to carry these messages do not work properly.

Irritable/Painful bladder: The symptoms of Irritable Bladder are basically the same as interstitial cystitis. Cystoscopy and biopsy results can reveal non-specific inflammation without the characteristic glomerulations (pin point bleeding) of an interstitial cystitis bladder.

Bladder Cancer: Cancer of the bladder.

Urinary stones: Stones in the urinary tract or bladder.

Bladder Neck Obstruction: is a cause of urinary disturbance that occurs by the narrowing or obstruction of the bladder neck (outlet) during voiding.

Bedwetting: Night urination in children or adults (a form of urinary incontinence, voiding while asleep)

Vesicoureteral Reflux: Urine normally flows in one direction—down from the kidneys, through tubes called ureters, to the bladder. Vesicoureteral reflux is the abnormal flow of urine from the bladder back into the ureters.

Urinary tract infections: Infection of the urinary system, usually bacterial.

Urinary tract infections (child): Infection of the urinary system in children.

Illustrative Method Used in Below Examples

NIRS monitoring shown below was achieved with the NIRO-300™ at a laser power of 1 mW, a pulse duration of 100 nsec, a pulse frequency of 2 kHz and a detector/emitter separation of 50 mm.

from center to center.

NIRS/Uroflow Tracings

NIRS tracings are related to physiological changes in a subject (i.e. detrusor contractions) prior to, during and following voiding. The changes in NIRS tracings are also consistent with the expected physiological changes associated with the detrusor muscle of the bladder and associated vessels and nerves. Furthermore, tracings obtained from subjects having bladder dysfunction are distinctly different between subjects having normal bladder function and between subjects known to have different dysfunctions. For example, a subject with a neurogenic bladder (i.e. FIG. 4B) has a distinctly different tracing than a subject having an obstruction resulting from an enlarged prostate (i.e. FIG. 3A). Traditional urodynamic analysis is based on pressure flow and weight voided by a subject (uroflow). The traditional methods do not measure bladder function directly and are often limited in the information provided. For example, a uroflow tracing is known to be limited by the delay in recording the weight of voided urine resulting from the directness of the flow to the recording surface.

Obstructed Bladder

Where the maximum flow rate and average flow rate are below the normal range, it could be due to obstruction, such as prostate enlargement or it could be due to a weak contraction of the bladder muscle itself. Using conventional techniques, without the use of the catheters to demonstrate the pressure flow curve (pdet) it would otherwise not be possible to comment on the cause of weak flow. On a standard uroflow curve no information is available until the patient begins to void and the determination of pdet values are invasive. In contrast, in the present embodiment, when a standard urodynamic tracing showing the urine flow rate (ml/sec), known as "uroflow", is shown adjacent an NIRS tracing as described herein for a patient with prolonged and fully intermittent uroflow curve, useful information may be obtained without the need for invasive procedures.

NIRS tracings provide data prior to urine appearing (voiding), and changes, which occur in the NIRS data are not apparent in the standard uroflow curve. In the 15 or so second period prior to voiding, Cyt becomes more oxidized indicating an increased energy demand by the cells in the bladder wall as intra-cellular oxygen acquires available electrons in greater proportion than the ensuing re-supply of substrate provided electrons. During this phase of increased proton pumping at the molecular level to increase energy production there is onset of a deficit of substrate in proportion to that of oxygen which is usually seen as a parabolic curve for Cyt indicating a decelerated rate of change in net redox status. Simultaneously, there is a decrease in $HbO_2$, Hb, and HbSum indicating a loss of blood volume due to the minor expulsion of blood brought about by a contraction of the detrusor to invoke urination. In this period, the loss of blood generally decreases the amount of oxygen available for use by Cyt and therefore limits and then reverses the change in net redox status.

When urination begins there is usually a significant rise in Hb, $HbO_2$ and HbSum, indicating that the internal pressure has decreased allowing the blood vessels to engorge, resulting in an increase in blood volume. The increasing blood volume serves to provide sufficient free oxygen to halt the Cyt change and brings about a balance between substrate electron supply and combining of oxygen to protons ($H_2O$). Gradually, the rate of change in NIRS hemoglobin parameters slows indicating less progress in the cascade of engorgement of smaller diameter blood vessels. This is likely due to an increasing tension of the detrusor that closes the urethral sphincter (thereby halting urine flow) in preparation for another detrusor contraction.

When there is no measure in the standard uroflow because the urinary stream has temporarily stopped due to the intermittent urine flow, the NIRS $HbO_2$, Hb, and HbSum parameters decrease as a muscle contraction occurs, prior to physically seeing more urine. Concurrently, there is a change in Cyt temporarily to a greater oxidation state, which eventually resolves.

The patient has further urinary flow and as the urine volume in the bladder decreases during this time, there is again an increase in the NIRS hemoglobin parameters as vessel engorgement follows from relaxing the tissue stretching within the bladder wall. During this same period, Cyt redox status becomes gradually more reduced with a greater proportion of Cyt molecules retaining electrons even though there is a greater abundance of oxygen available for transfer, thereby indicating a lowered energy demand (ATP synthesis) than during the contraction phase.

As the patient's bladder continues to empty, there is continued increase in blood volume in the wall of the bladder as the NIRS data continue to demonstrate physiologic measurements within the bladder wall even though there is no more information from the uroflow data. As the bladder has finished contracting and it is in a more relaxed state, blood volume can continue to increase in the bladder muscle wall as progressively smaller vessels continue to relax and become engorged. This cascade reflects differences in the contributions of large and small vessels, since different vessel diameters have differing sphincter compliance and therefore cannot simultaneously open sufficiently to restore blood flow simultaneously. As above Cyt levels continue to indicate a lowered energy demand.

The observed NIRS patterns of change are physiologically logical and indicate typical bladder tissue compliance. In contrast, conventional uroflow analysis confirms only a prolonged, intermittent flow.

Normal Bladder

A standard urodynamic tracing indicates normal uroflow with voiding of 150-1000 cc with no residual volume. NIRS indicates that there is an increase in blood volume with relaxation of the detrusor as urination is underway. Once peak flow occurs, there is a slight detrusor contraction to maintain the peak flow, after which there is a prolonged gradually increasing detrusor contraction until voiding is complete. This latter contraction is gentler than that used to sustain peak flow in that it is of the same magnitude, but requires twice the duration to achieve that magnitude of change.

EXAMPLES

NIRS/Uroflow/Pressure Tracings

Figure 3A:
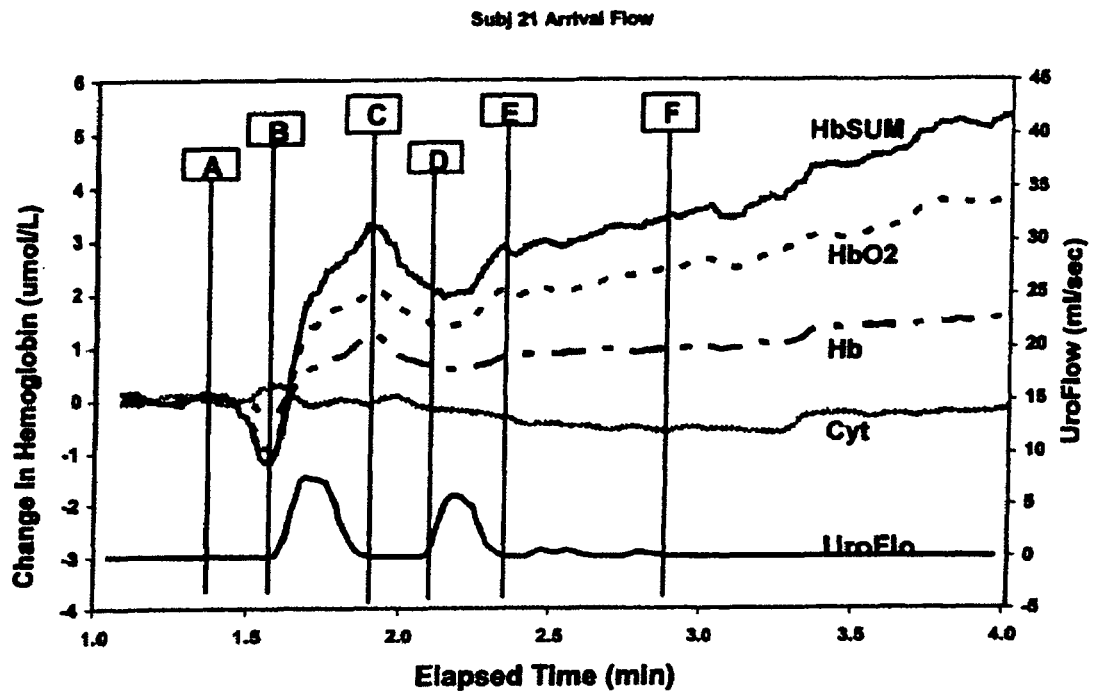
FIG. 3A is a urodynamic tracing of Uroflow Patient #21 showing detrusor over activity and voiding pressure within the lower range of normal in an 82 year old male with a history of angina and Type II diabetes, with complaints of frequency, nocturia x3, and prostate enlargement (BPH).

FIG. 3A—Uroflow Patient #21 (Example of Detrusor over Activity and Voiding Pressure within the Lower Range of Normal)

An 82 year old male with a history of angina and Type II diabetes, with complaints of frequency, nocturia x3, and prostate enlargement (BPH). The patient was not receiving medication specifically for bladder treatment.

The standard urodynamic tracing is shown at the bottom of the graph and represented by the "uroflow" tracing. The patient arrived with a full bladder. The patient has a prolonged and fully intermittent uroflow curve. The maximum flow rate and average flow rate are below the normal range. This could be due to obstruction, such as prostate enlargement or it could be due to a weak contraction of the bladder muscle itself. Using conventional techniques, without the use of the catheters to demonstrate the pressure flow curve, it would not otherwise be possible to comment on the weak flow. However, in the present example, with the NIRS tracing, a noninvasive means for determining the cause of the weak flow is available. The total voided volume is 121 cc. The residual urine was determined by catheter as 65 cc. No information is available from the standard uroflow curve until point B, where the patient begins to void.

The NIRS tracings are shown for the same patient beginning 15 seconds prior to urine appearing (point B), changes are occurring in the NIRS data (from A to B) that are not apparent in the standard uroflow curve. In this 15 second period, Cyt becomes more oxidized indicating an increased energy demand by the cells in the bladder wall as intracellular oxygen acquires available electrons in greater proportion then the ensuing re-supply of substrate provided electrons. During this phase of increased proton pumping at the molecular level to increase energy production there is onset of a deficit of substrate in proportion to that of oxygen which is seen as the parabolic shape of the Cyt curve indicating a decelerated rate of change in net redox status. Simultaneously, there is a decrease in $HbO_2$, Hb, and HbSum indicating a loss of blood volume due to the minor expulsion of blood brought about by a contraction of the detrusor to invoke urination. In this period, the loss of blood decreases the amount of oxygen available for use by Cyt and therefore limits and then reverses the change in net redox status, as seen briefly immediately after point B.

When urination begins at point B, there is a significant rise in Hb, $HbO_2$ and HbSum, indicating that the internal pressure has decreased allowing the blood vessels to engorge, resulting in an increase in blood volume (B to C). The increasing blood volume serves to provide sufficient free oxygen to halt the Cyt change (apparent briefly after point B) and brings about a balance between substrate electron supply and combining of oxygen to protons ($H_2O$). Midway between B and C the rate of change NIRS hemoglobin parameters slows indicating less progress in the cascade of engorgement of smaller diameter blood vessels. This is likely due to an increasing tension of the detrusor that closes the urethral sphincter (thereby halting urine flow) in preparation for another detrusor contraction.

Between points C and D, there is no measure in the standard uroflow because the urinary stream has temporarily stopped. However, the NIRS $HbO_2$, Hb, and HbSum parameters decrease between points C and D, as a muscle contraction occurs, similar to that described above from A to B, prior to physically seeing urine at point D. Concurrently, there is a change in Cyt temporarily to a greater oxidation state which resolves in the same manner as described above at point B.

The patient has further urinary flow between D and E, and as the urine volume in the bladder decreases during this time, there is again an increase in the NIRS hemoglobin parameters as vessel engorgement follows from relaxing the tissue stretching within the bladder wall. During this same period, Cyt redox status becomes gradually more reduced with a greater proportion of Cyt molecules retaining electrons even though there is a greater abundance of oxygen available for transfer, thereby indicating a lowered energy demand (ATP synthesis) than during the contraction phase (C to D).

As the patient's bladder continues to empty between E and F, there is continued increase in blood volume in the wall of the bladder as the NIRS data continue to demonstrate physiologic measurements within the bladder wall even though there is no more information from the uroflow data. We hypothesize that during this time, when the bladder has finished contracting and it is in a more relaxed state, blood volume can continue to increase in the bladder muscle wall as progressively smaller vessels continue to relax and become engorged. This cascade reflects differences in the contributions of large and small vessels, since different vessel diameters have differing sphincter compliance and therefore cannot simultaneously open sufficiently to restore blood flow simultaneously. As with the previous period (D to E), Cyt continues to indicate a lowered energy demand.

The observed NIRS patterns of change in this patient are physiologically logical and indicate typical bladder tissue compliance. NIRS indicates that muscle contraction energy demand is about 10% of normal and requires twice as long a duration as normal to initiate urination. NIRS also indicates that muscle tension/relaxation cannot be sustained during voiding thereby resulting in intermittent urine flow. Conventional uroflow analysis confirms only a prolonged, intermittent flow.

Figure 3B:
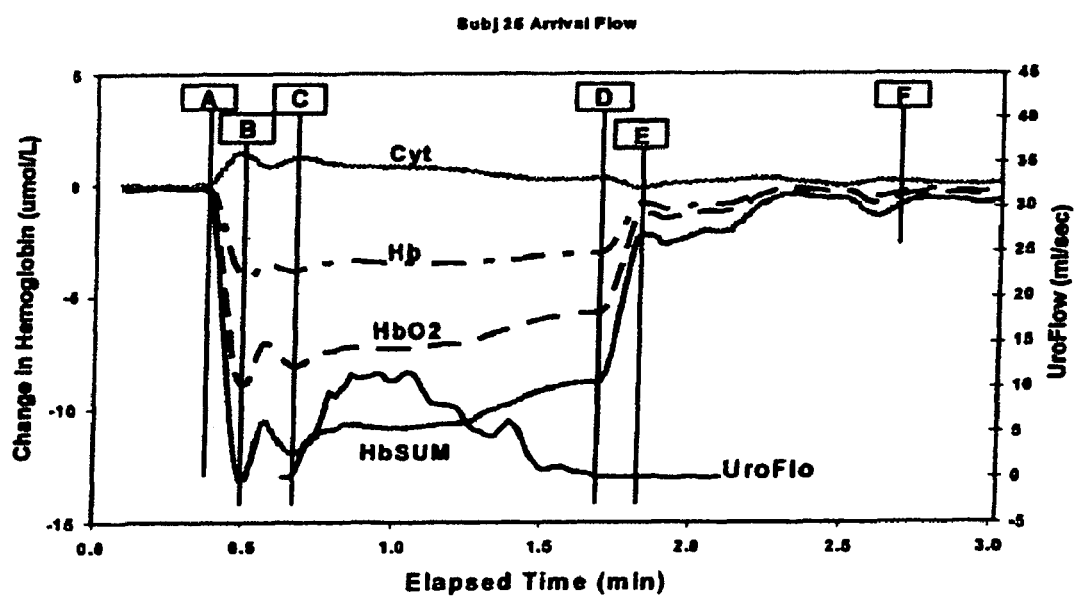
FIG. 3B is a urodynamic tracing of Uroflow Patient #25 showing normal uroflow, detrusor over activity, urgency incontinence, and normal pressure flow in a 62 year old female with a history of urgency frequency and urgency incontinence.

FIG. 3B—Uroflow Patient #25: (Example of Normal Uroflow, Detrusor over Activity, Urgency Incontinence, and Normal Pressure Flow)

A 62 year old female with a history of urgency frequency and urgency incontinence.

The standard urodynamic tracing indicates that the patient has a prolonged uroflow curve. The total voided volume is 360 cc. The patient was subsequently catheterized to remove a residual of 55 cc of urine.

NIRS indicates that from points A to B, Hb, $HbO_2$ and HbSum decrease as the muscle contracts and blood is pressed out of the bladder wall. Cyt becomes more oxidized, indicating that the muscle is using more oxygen to meet the energy demand of contraction to initiate flow. At C, urination begins, with commensurate gradual increase in blood volume (HbSum, $HbO_2$ and Hb) and a gradual reduction in Cyt, indicative of relaxation of the bladder wall. Between D and E, there is a significant increase in blood volume, which likely reflects total relaxation of the bladder with return of blood flow. Cyt also becomes more reduced between D and E, which supports the perception of the relaxation of the bladder muscle. Between E and F, NIRS continues to collect data on the status of the bladder, although standard Urodynamics is not able to obtain any additional information. The observed NIRS patterns of change in this patient are physiologically logical and indicate typical bladder tissue compliance. The detrusor muscle tension is maintained constant through the period of peak flow, then diminishes gradually during completion of urination and becomes quickly relaxed at the completion of urination.

Figure 4A:
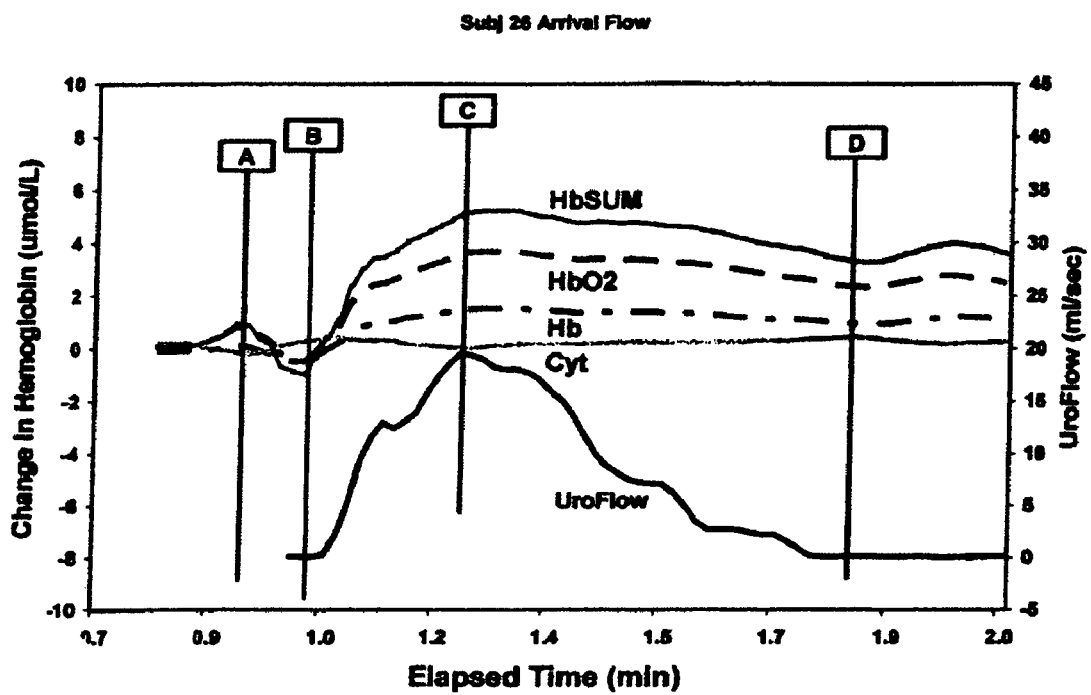
FIG. 4A is a urodynamic tracing of Uroflow Patient #26 showing normal uroflow and detrusor over activity in a 67 year old female with a history of frequency, urgency and incontinence.

FIG. 4A—Uroflow Patient #26 (Example of Normal Uroflow and Detrusor over Activity)

67 year old female with a history of frequency, urgency and incontinence (not stress incontinence)

The standard urodynamic tracing indicates that this is a good uroflow in a female. The patient has a normal-shaped uroflow curve. The maximum flow is 20 cc per sec, with an average of 10 cc per sec. The voided volume is 411 cc, and there was a residual of 45 cc.

NIRS indicates that between points A and B, there are a decrease in Hb, $HbO_2$, and HbSum and increase in net Cyt oxidized redox state with detrusor contraction in preparation for voiding. At point B, urination begins and blood volume increases as the bladder muscle relaxes. Between C and D, effort to empty the remainder of the urine begins, blood volume decreases as the muscle contracts, and Cyt becomes more oxidized with the energy demand (a slower, but similar pattern to that seen between A and B). At D, the bladder is empty, and the standard uroflow data stops. NIRS data continues, and shows an increase in blood volume as the bladder muscle relaxes. Cyt becomes slightly more reduced as the energy demand decrease.

The observed NIRS patterns of change in this patient are physiologically logical and indicate typical bladder tissue compliance. Once urination is underway for 6 seconds there is an increase in detrusor tension that becomes sustained at the peak of urine flow and thereafter progressively increases slightly until the bladder becomes empty.

Figure 4B:
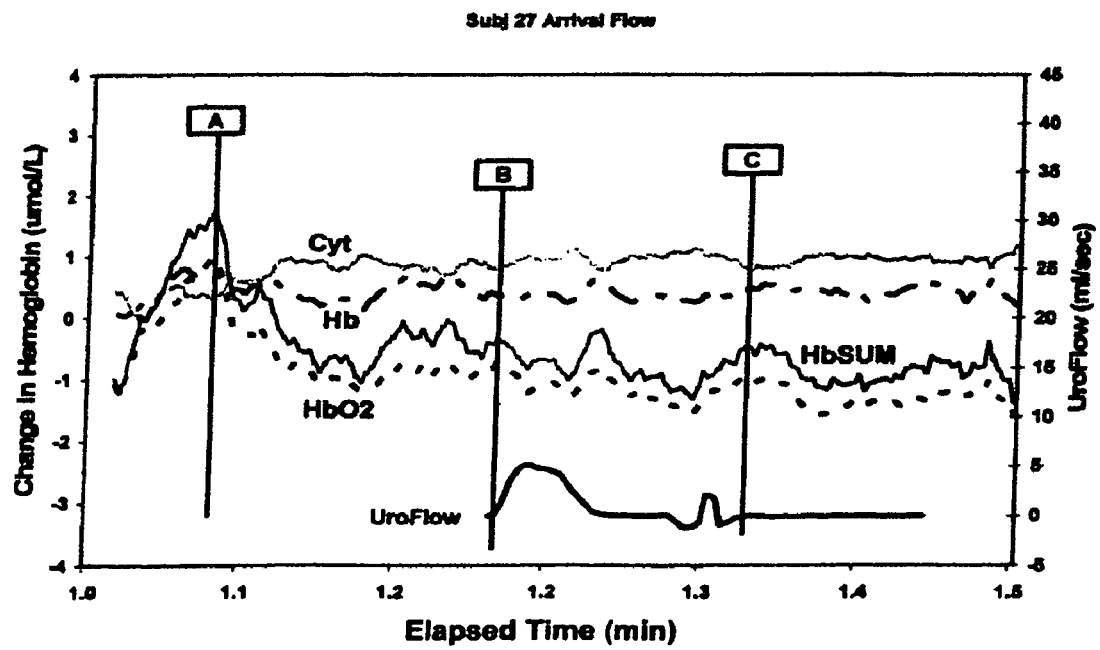
FIG. 4B is a urodynamic tracing of Uroflow Patient #27 showing neurogenic bladder in a 72 year old male with a history of spinal cord injury.

FIG. 4B—Uroflow Patient #27 (Example of Neurogenic Bladder)

72 year old male with a history of spinal cord injury.

The standard urodynamic tracing indicates the maximum flow is 7 with an average flow of 4 cc per sec. The voided volume was 74 cc with a residual of 100 cc.

NIRS indicates a data collection that is less smooth than typical data sets. The bladder may be in spasm. Nevertheless, the typical NIRS voiding pattern is apparent. Between A and B, the patient is attempting to initiate the stream, and blood volume (HbSum, $HbO_2$ and Hb) decrease as the muscle contracts and Cyt becomes more oxidized as the energy demand increases. At B, a small amount of urination begins. Unlike in other patients in whom the blood volume increases at this point, blood volume continues to decrease as the patient continues to voluntarily contract the bladder muscle. There is a period of small increase between B and C, which likely relates to a short period of relaxation. Just prior to C, when the patient indicates that he is finished, blood volume increases and Cyt becomes more reduced as the bladder muscle relaxes.

The observed NIRS patterns of change in this patient are physiologically logical and indicate a good tissue compliance corresponding to good rates of change. Detrusor contraction energy demand is 25% of normal and is 1.6 times slower to evolve than normal. The start of urine flow is augmented by a slightly increasing detrusor contraction that is steadily maintained at the peak of flow, then there is a brief increase in contraction before relaxing until flow ceases, and then a prolonged increase in contraction again until some of the residual volume is also expelled, after which the detrusor relaxes and there is no further voiding.

Figure 5A:
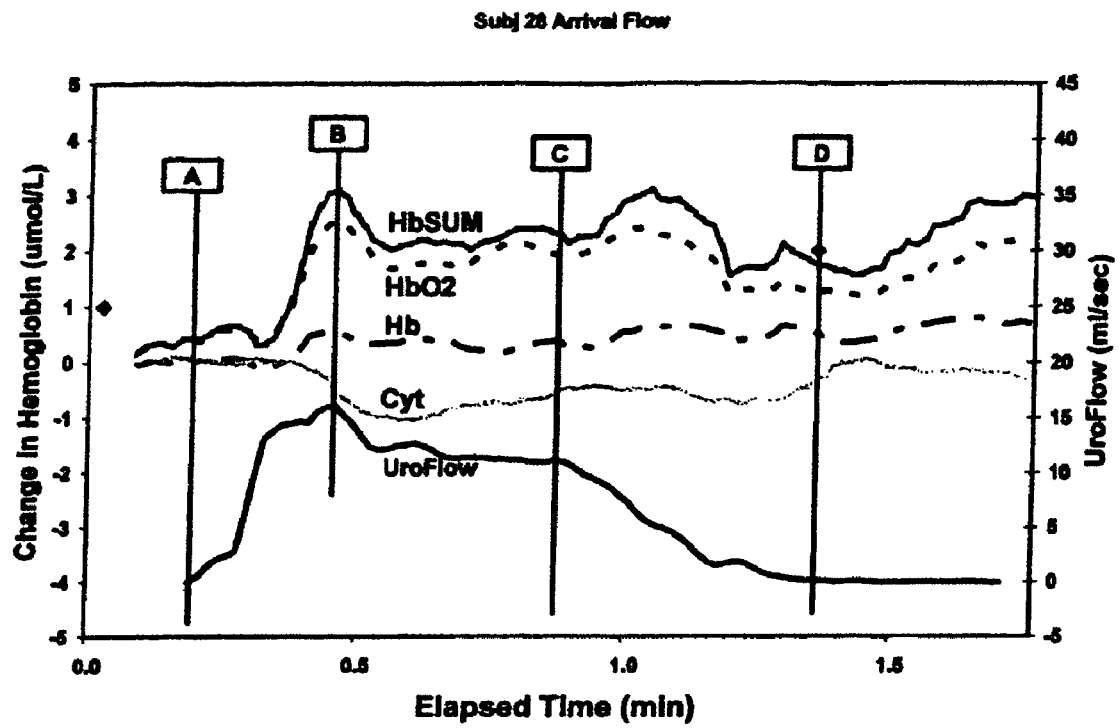
FIG. 5A is a urodynamic tracing of Uroflow Patient #28 showing prolonged uroflow (but almost normal in a 34 year old female with a history of frequency, interstitial cystitis and no history of incontinence.

FIG. 5A—Uroflow Patient #28 (Example of a Prolonged Uroflow (But Almost Normal)

34 year old female with a history of frequency. There is no history of incontinence. There is a history of interstitial cystitis.

The standard urodynamic tracing indicates a reasonable uroflow. Maximum flow 14 cc, average 9 cc/sec Voided volume was 212 cc, residual volume was 5 cc.

NIRS indicates that between A and B, blood volume increases (HbSum, Hb, $HbO_2$) steeply as the bladder muscle relaxes and Cyt becomes more reduced as the energy demand from the muscle decreases. Between B and D, there are several waves that indicate muscle contraction and relaxation cycles. Although Hb is changing, the magnitude is reduced compared with other patients. When urination is complete, blood volume continues to rise gradually, and Cyt initially becomes more oxidized and then more reduced. There appears to be a delay of about 10 seconds in the pattern of Cyt changes compared with other patients. The changes in Cyt are also more gradual throughout. This likely reflects differences in pathology.

The observed NIRS patterns of change in this patient are physiologically logical and indicate typical bladder tissue compliance. Once peak flow occurs there is a refreshing of the detrusor contraction that is maintained steadily to continue the flow. As the bladder approaches being empty there is further contraction which is held briefly and then relaxed once the bladder is empty.

Figure 5B:
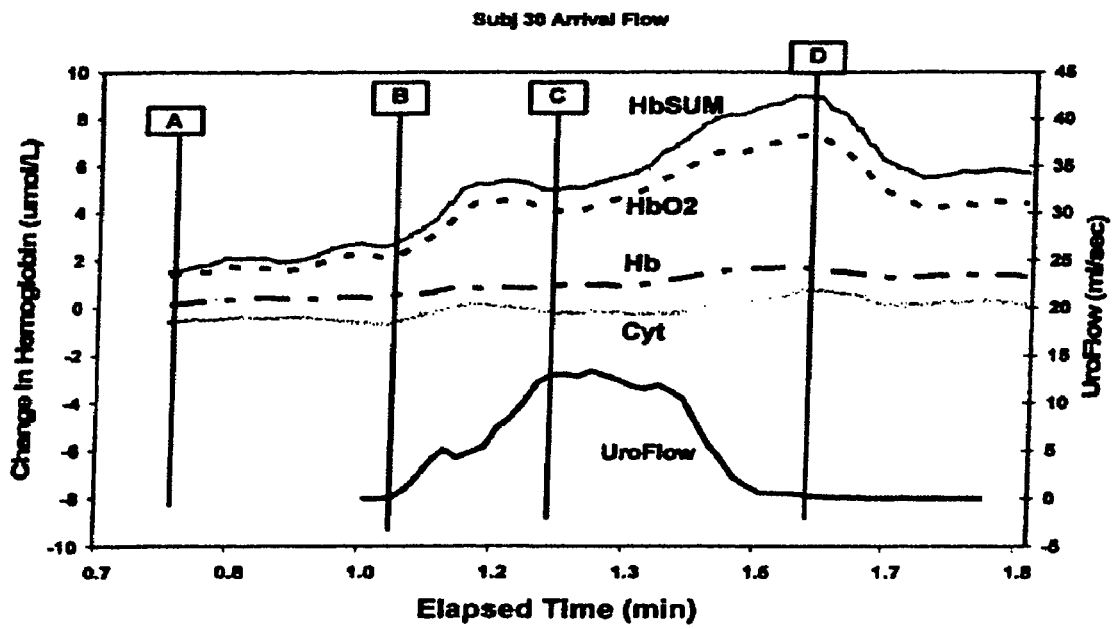
FIG. 5B is a urodynamic tracing of Uroflow Patient #30 showing a slow onset of uroflow in a 30 year old female who has a history of urgency and frequency and some incontinence.

FIG. 5B—Uroflow Patient #30 (Example of a Slow Onset of Uroflow)

30 year old female who has a history of urgency and frequency and some incontinence.

The standard urodynamic tracing indicates that the patient has a prolonged uroflow curve. The maximum flow is 17 cc, with an average flow of 9 cc. The total voided was 469 cc, with a residual of 50 cc.

NIRS indicates a pattern of change that is substantially different from others. Between A and B, there is a small amount of increase in $HbO_2$ prior to initiating the stream. As the urine stream increases between B and C, there is a faster increase in $HbO_2$. There is essentially no change in volume of Hb throughout. There is a concurrent small increase in the oxidation level of Cyt, which again is unlike patients without urgency. Between C and D, the bladder muscle appears to relax, with an increase in HbSum, with a much smaller increase in Hb. At D, after urination has stopped, there is a decrease in HbSum, which may reflect a final voluntary contraction to try to expel the residual. However, the Cyt becomes more reduced. This likely reflects a pathologic condition, in that the oxygen supply and demand are not balanced, possibly as a result of historical damage to the venous vessels.

The observed NIRS patterns of change in this patient are physiologically logical and indicate typical bladder tissue compliance with respect to the magnitudes of change. NIRS indicates passive voiding without the use of detrusor contraction, although there is some contraction just prior to peak flow; and, there is a more significant contraction, once voiding is finished, in order to curtail dribbling leakage of the residual urine.

Supine Filling Cystometrograms (CMG's)

Figure 6A:
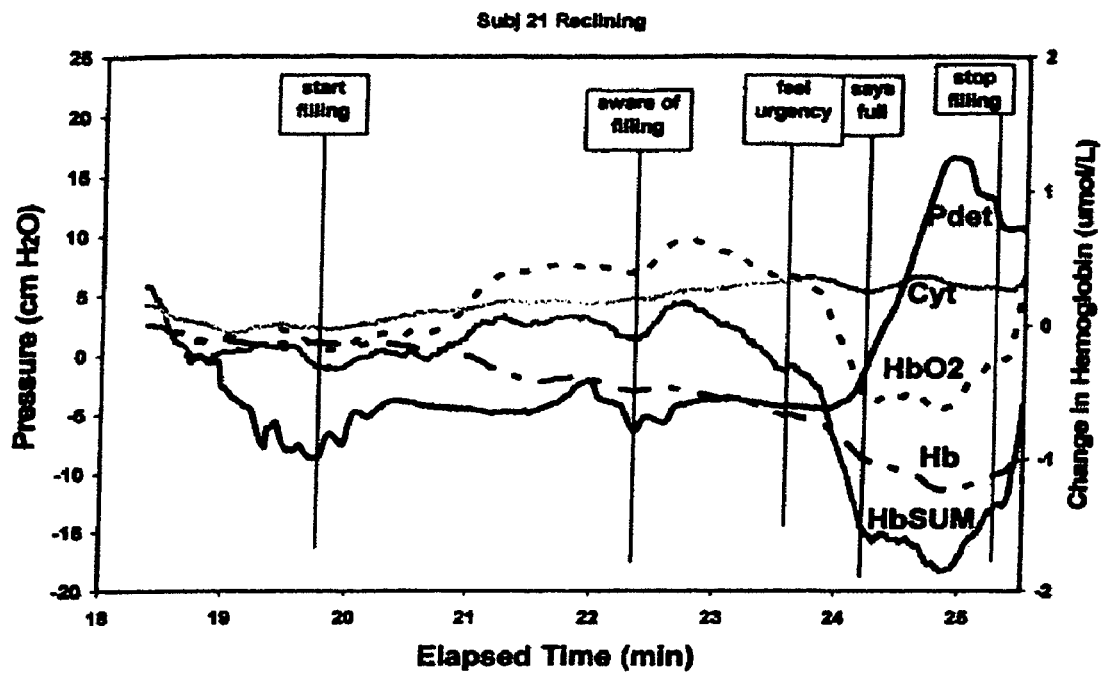
FIG. 6A is a urodynamic tracing of Supine CMG Patient #21 showing low contraction pressure with low flow due to obstruction in an 82 year old male with a history of angina and Type II diabetes, with complaints of frequency, nocturia x3, and prostate enlargement (BPH).

FIG. 6A—Supine Patient #21 (Example of Low Contraction Pressure with Low Flow Due to Obstruction)

An 82 year old male with a history of angina and Type II diabetes, with complaints of frequency, nocturia x3, and prostate enlargement (BPH). No meds specifically for bladder treatment.

The standard urodynamic tracing indicates that PDet, which is a reflection of the pressure in the bladder caused by the bladder muscle, shows that at Elapsed time 22, just before the patient indicates that he is aware of bladder filling, there is an unstable bladder contraction (peak in PDet) which then spontaneously resolves. Shortly after, the patient felt urgency, the bladder pressure began to rise, and the patient indicated that the bladder was at maximum capacity at the point "says full".

NIRS indicates that as the bladder is filled, $HbO_2$ rises and Hb decreases somewhat. There is a period of stability until the patient becomes aware of filling just after the unstable bladder contraction. At this point, there is a small steep rise in $HbO_2$. Beyond this, $HbO_2$ decreases, with a change in, the rate of decrease after the patient reports feeling urgency. Note that there is a short plateau at the point that the patient reports awareness of filling and urgency. $HbO_2$ stabilizes after the patient says he is full. There is a consistent decrease in Hb as the bladder wall is stretched and thinned to accommodate the increased volume.

Figure 6B:
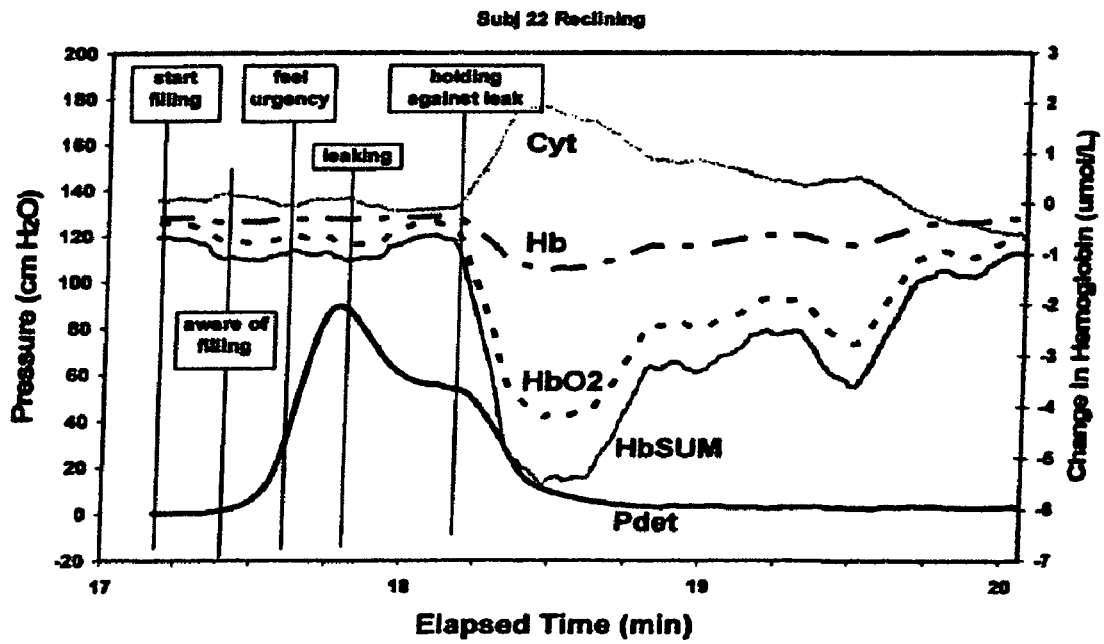
FIG. 6B is a urodynamic tracing of Supine CMG Patient #22 showing a high contraction pressure with low flow in a 65 yr old male with obstruction and urgency incontinence.

FIG. 6B—Supine Patient #22 (Example of High Contraction Pressure with Low Flow Due to Obstruction)

A 65 yr old male with obstruction and urgency incontinence.

The standard urodynamic tracing indicates that the patient has urgency and the PDet graph indicates that there is detrusor overactivity.

NIRS indicates that as the bladder begins filling, there is a slight decrease in $HbO_2$ and in HbSum. Throughout this period, Hb remains constant. The patient becomes aware of filling at the point at which $HbO_2$ and HbSum stabilize and Cyt begins to become more reduced. The patient feels urgency and begins involuntary leaking (urgency incontinence). As the bladder pressure falls due to leakage, the patient begins to trying to hold his urine against the involuntary leak. $HbO_2$ and HbSum return to baseline. After holding against the leakage for a few seconds, the patient actively urinates past the catheter, and the effort decreases the blood volume in the bladder wall and Cyt becomes more oxidized, indicating energy expenditure. $HbO_2$ and HbSum decrease sharply, and Hb decreases. As the patient holds against the leak, the detrusor pressure (PDet) decreases. Cyt begins a gradual return to baseline as PDet plateaus and $HbO_2$ and HbSum return to baseline.

Figure 7A:
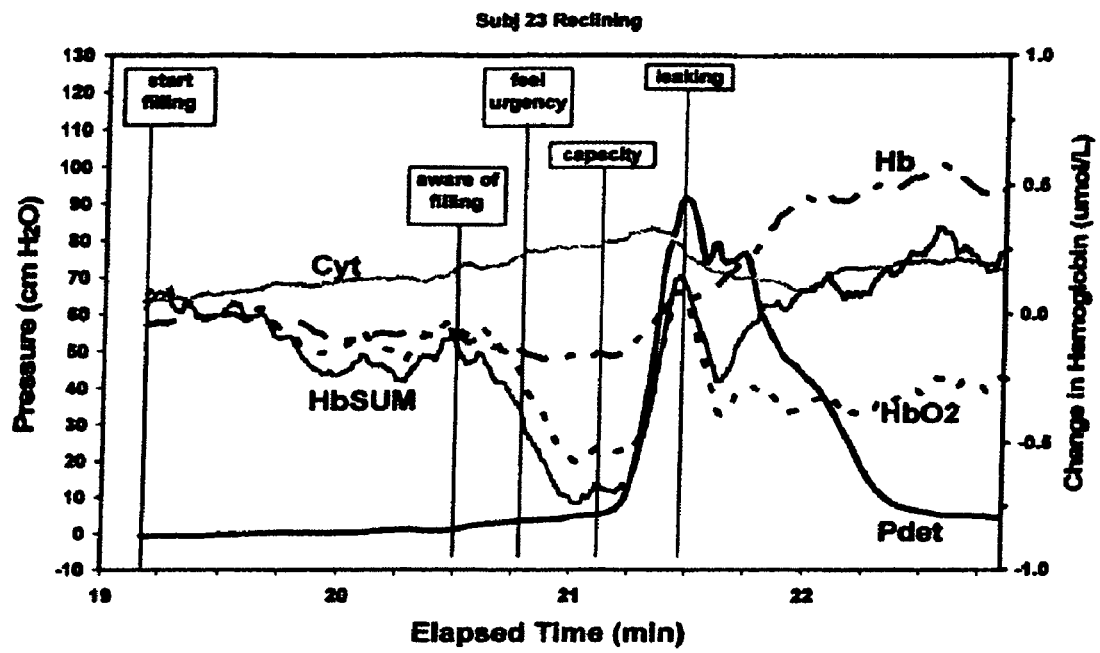
FIG. 7A is a urodynamic tracing of Supine CMG Patient #23 showing detrusor over activity, urgency incontinence, high contraction pressure, and obstruction in a 55 year old male with reduced flow, urinary frequency, post-void dribbling.

FIG. 7A—Supine Patient #23 (Example of Detrusor over Activity, Urgency Incontinence, High Contraction Pressure, and Obstruction)

This is a 55 year old male with reduced flow, urinary frequency, post-void dribbling.

The standard urodynamic tracing indicates that there is a very gradual increase in detrusor pressure with filling, which is within the normal range. Detrusor pressure rises rapidly after the patient indicates he is at capacity until leakage is seen at a pressure of approximately 90 cm $H_2O$.

NIRS indicates that from the start of filling to awareness of filling, there is a gradual decrease in Hb $HbO_2$ and HbSum and a gradual increase in the oxidation of Cyt. Just after the patient indicates awareness of filling, $HbO_2$ and HbSum decrease sharply, and continue to decrease rapidly until the patient indicates that he is at capacity. Interestingly, in this patient, there is nothing noteworthy at the point at which he indicates that he feels urgency. Shortly after the patient indicates that he is at capacity, $HbO_2$ and HbSum rise precipitously while Cyt continues to become more oxidized. Throughout this period, Hb has decreased very gradually. Hb begins to rise just after capacity is reached, which, along with the rise in $HbO_2$ indicates a sudden increase in blood volume. Just before leakage begins, Cyt begins to become more reduced, indicating a decrease in energy available in the muscle. HbSum and Cyt return to baseline as PDet returns to baseline with a net decrease in oxygenation ($HbO_2$ decreased and Hb increased).

Figure 7B:
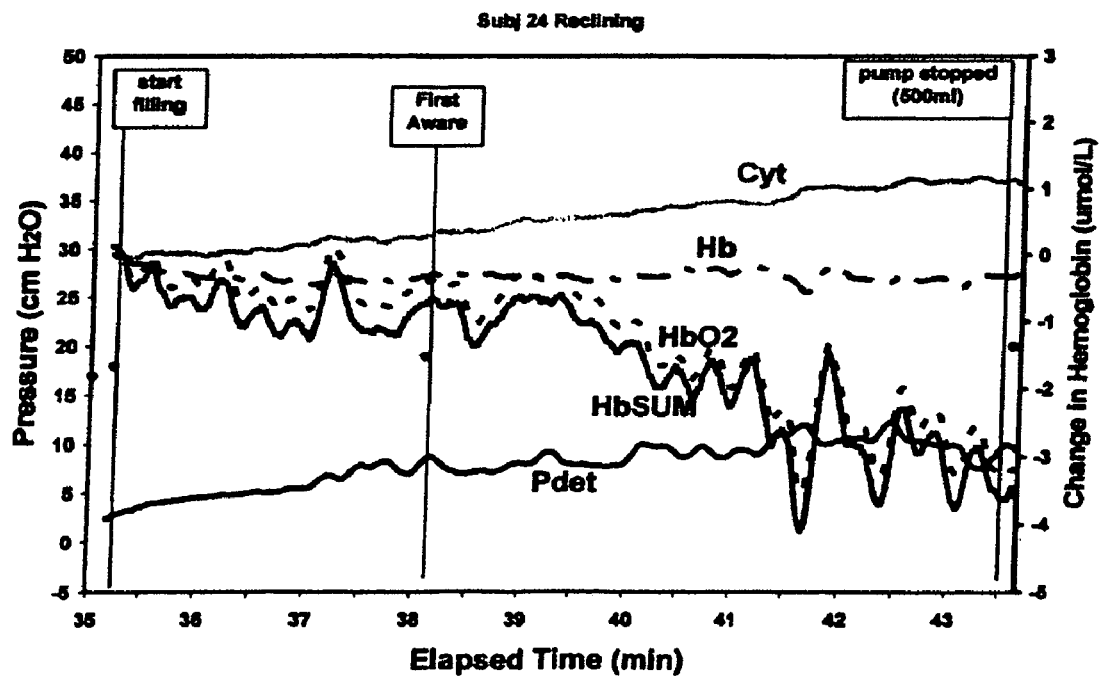
FIG. 7B is a urodynamic tracing of Supine CMG Patient #24 showing no voluntary detrusor contraction in a 65 yr male with no voluntary detrusor contraction, and overflow incontinence.

FIG. 7B—Supine Patient #24 (Example of having no Voluntary Detrusor Contraction)

A 65 yr male with no voluntary detrusor contraction, and overflow incontinence. The patient feels a possible first sensation at 173 cc, but he never reaches a sensation of urgency or capacity, despite 500 cc (maximum safe infusion limit) in the bladder.

The standard urodynamic tracing indicates that the bladder spasms seen in the PDet are reflected in the NIRS changes in $HbO_2$ as the detrusor muscle contracts and relaxes intermittently, pressing blood out of the muscle and then allowing blood to return to the muscle.

NIRS indicates overall, that as PDet and bladder volume increase with filling, blood volume in the bladder muscle decreases, consistent with thinning of the bladder wall and consequent narrowing of the vessels. Cyt gradually becomes increasingly oxidized throughout while Hb remains constant. We hypothesize that this indicates that the cascade of electron transfer is slowed likely because of a lack of substrate (because the bladder does not have stores of substrate).

Figure 8A:
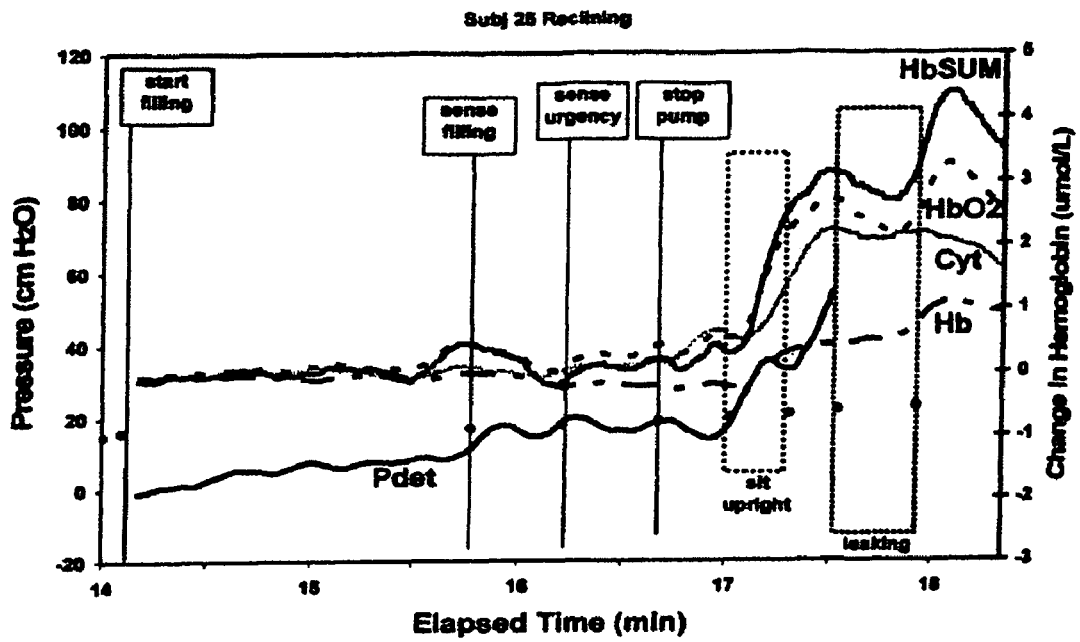
FIG. 8A is a urodynamic tracing of Supine CMG Patient #25 showing normal uroflow, detrusor over activity, urgency incontinence, and normal pressure flow in a 62 year old female with a history of urgency frequency and urgency incontinence.

FIG. 8A—Supine Patient #25 (Example of Normal Uroflow, Detrusor over Activity, Urgency Incontinence, and Normal Pressure Flow)

A 62 year old female with a history of urgency frequency and urgency incontinence.

NIRS indicates that throughout the period of filling there is no significant change in any of the NIRS parameters. Changes do occur when the patient sits upright, but these may be artefact, since when the patient changes position, the bladder changes both shape and position. When the patient unavoidably leaks (incontinence) past the catheter, $HbO_2$ and HbSum decrease while Hb remains stable. Cyt becomes more reduced initially, and then stabilizes. The bladder relaxes as voiding comes to an end, and blood volume increase. Following leakage, the detrusor pressure begins to rise again, and with this increase, the blood volume again decreases.

Figure 8B:
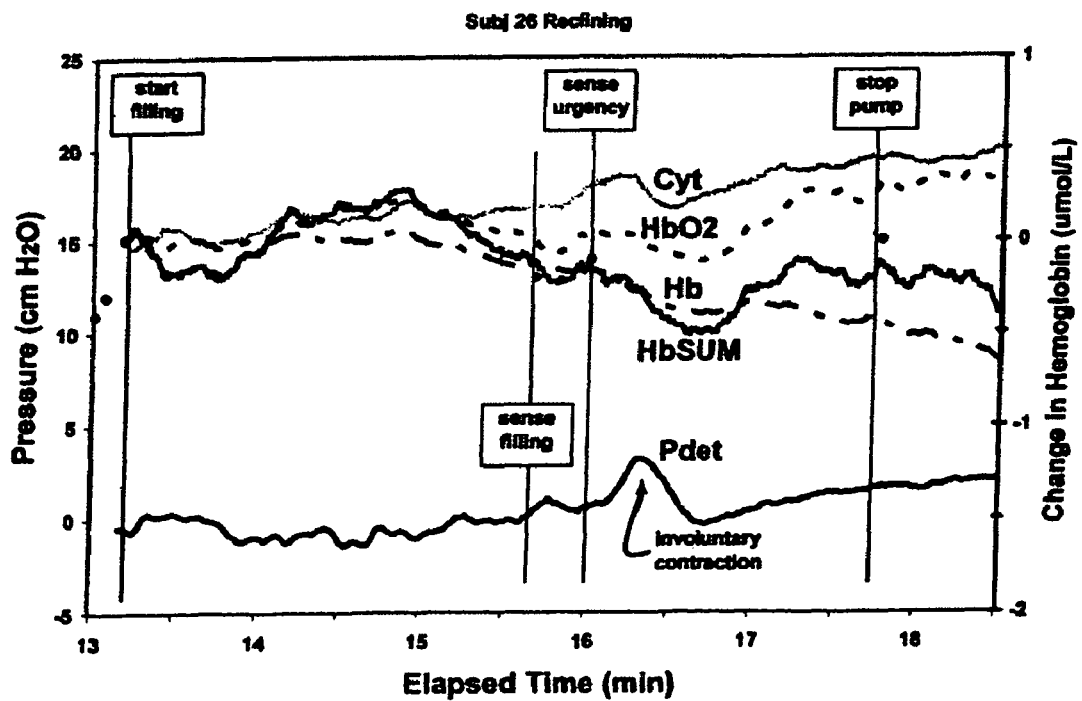
FIG. 8B is a urodynamic tracing of Supine CMG Patient #26 showing normal uroflow and detrusor over activity in a 67 year old female with a history of frequency, urgency and incontinence, but not stress incontinence.

FIG. 8B—Supine Patient #26 (Example of Normal Uroflow and Detrusor over Activity)

67 year old female with a history of frequency, urgency and incontinence (not stress incontinence)

The standard urodynamic tracing indicates that the detrusor pressure is quiet during filling, with the exception of one minor increase in detrusor pressure just following first urge.

NIRS indicates that the oxygenation parameters are stable throughout. This is a near normal patient. However, there is a small decrease in blood volume, as the pressure in the detrusor increases. Following the one contraction (increase in detrusor pressure), blood volume returns to baseline. This small change may indicate that there is little change in the bladder wall thickness, or in the compliance of the vessels in this patient. This patient did not reach "capacity".

CMG Sitting and Pressure Flow

Figure 9A:
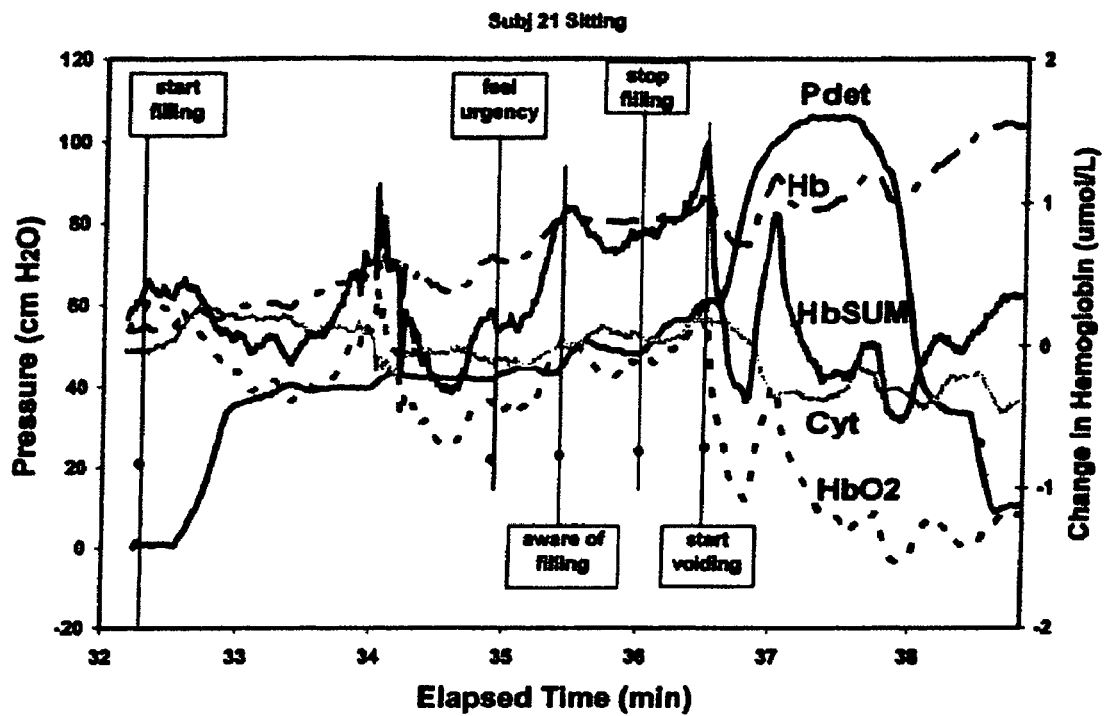
FIG. 9A is a urodynamic tracing of Sitting CMG Patient #21 showing poor muscle compliance in an 82 year old male with a history of angina and Type II diabetes, with complaints of frequency, nocturia x3, and prostate enlargement (BPH).

FIG. 9A—Upright Patient #21 (Example of Poor Muscle Compliance)

An 82 year old male with a history of angina and Type II diabetes, with complaints of frequency, nocturia x3, and prostate enlargement (BPH). No meds specifically for bladder treatment.

The standard urodynamic tracing indicates the pressure flow study begins at the "Start Voiding" point. In this patient, PDet initially rises to almost 110 cm $H_2O$ before returning to near baseline.

NIRS indicates that there is a very sharp decrease in $HbO_2$, Hb, and HbSum as the bladder muscle contracts. There is a subsequent rise in $HbO_2$ and Hb indicating a relaxation, followed by another contraction with decrease in $HbO_2$. However, Hb begins to rise gradually, indicating that the muscle is beginning to relax. There are several smaller bladder contraction/relaxation cycles seen as the bladder nears empty. Cyt initially becomes more reduced and then stabilizes, likely coincident with the initial energy demand of the contraction.

Figure 9B:
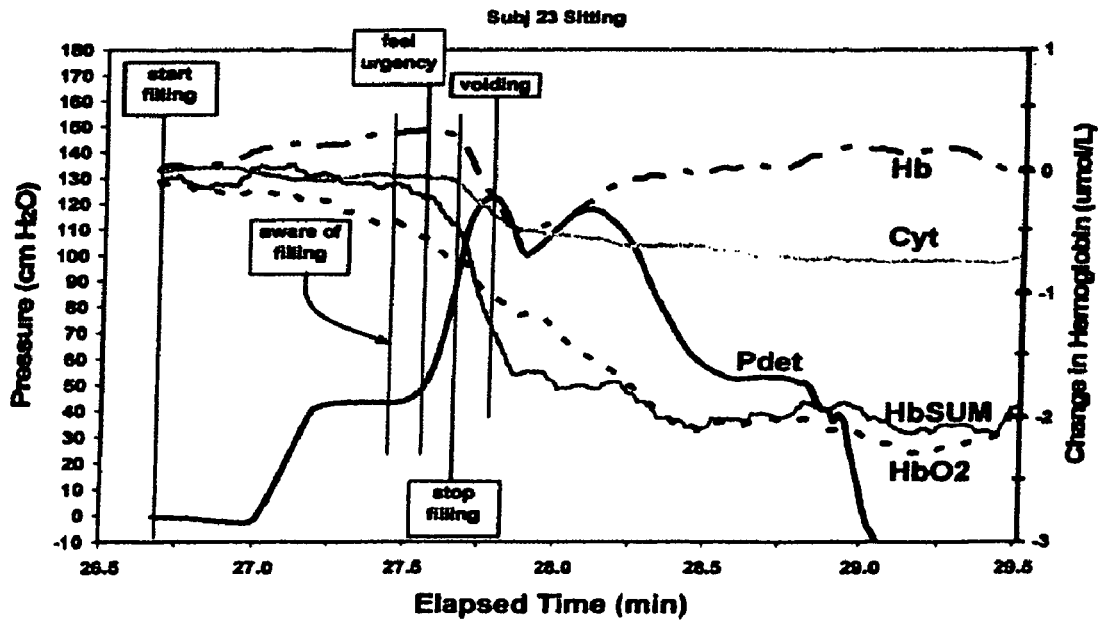
FIG. 9B is a urodynamic tracing of Sitting CMG Patient #23 showing detrusor over activity, urgency incontinence, high contraction pressure, and obstruction in a 55 year old male with reduced flow, urinary frequency, post-void dribbling.

FIG. 9B—Upright Patient #23 (Example of Detrusor over Activity, Urgency Incontinence, High Contraction Pressure, and Obstruction)

This is a 55 year old male with reduced flow, urinary frequency, post-void dribbling.

The standard urodynamic tracing indicates that right after the patient feels first urge, there is detrusor over activity and a marked rise in pressure. He is not able to suppress the bladder contraction, and voiding begins. At this time, there is a coincidental fall in bladder pressure with voiding.

NIRS indicates that there is a gradual decline in $HbO_2$ throughout the study, until PDet returns to approximately the level at which the patient initially felt urgency, following which, blood volume remains constant. Cyt initially becomes more reduced when filling stops, and then stabilizes as voiding commences. Hb begins to increase shortly after voiding commences.

Figure 10A:
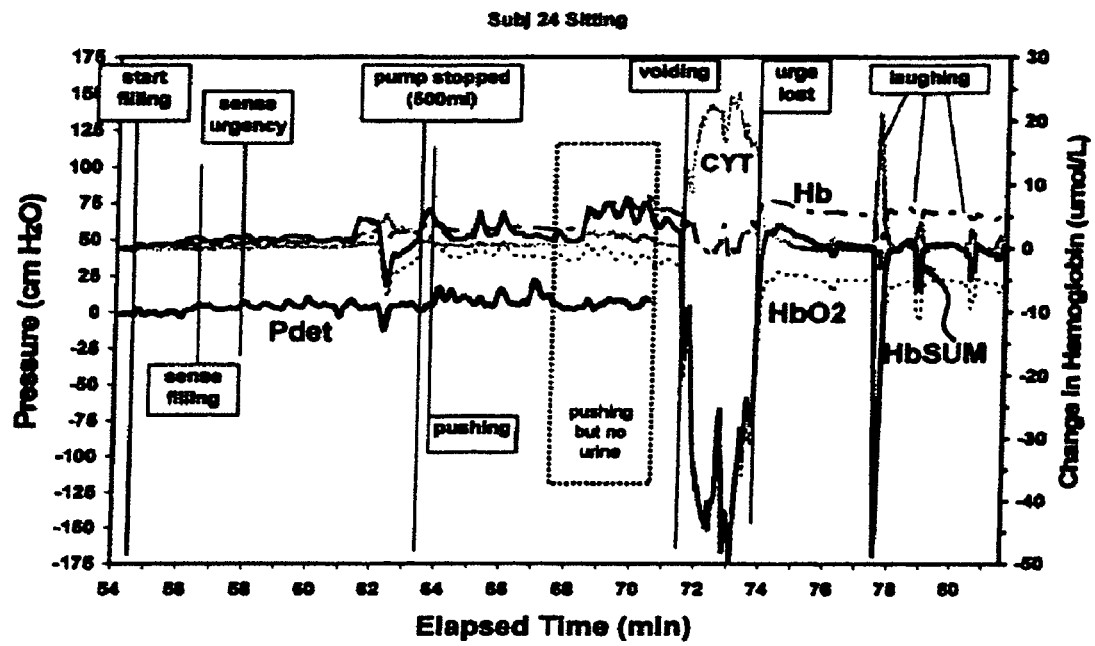
FIG. 10A is a urodynamic tracing of Sitting CMG Patient #24 showing no voluntary detrusor contraction in a 65 yr male with no voluntary detrusor contraction, and overflow incontinence.

FIG. 10A—Upright Patient #24 (Example of having no Voluntary Detrusor Contraction)

A 65 yr male with no voluntary detrusor contraction, and overflow incontinence.

The standard urodynamic tracing indicates that repeat CMG in the sitting position again shows poor bladder sensation.

NIRS indicates that when the patient attempts to void, there is no significant detrusor contraction, and the patient attempts to void by abdominal straining. This is reflected in the relatively flat Pdet line, and a marked increase in abdominal straining is noted by NIRS as he attempts to force the urine out ("pushing"). No actual flow is seen. During the straining, (dotted box) there are intermittent increases and decreases in NIRS, possibly reflecting effect of the pressure from the abdominal straining on the blood volume in the detrusor muscle. When the patient actually voids, there is a dramatic decrease in blood volume in the detrusor and an increase in the oxidation level of Cyt, indicative of the increased energy demand. NIRS data return to baseline when the urge to void passes.

Figure 10B:
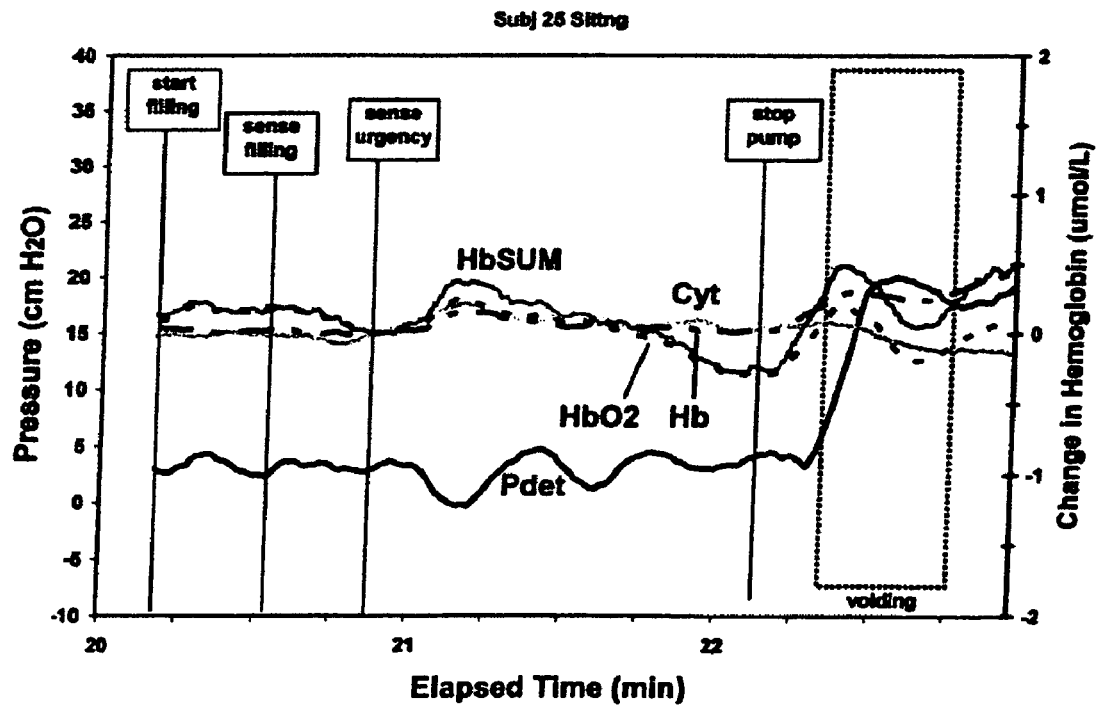
FIG. 10B is a urodynamic tracing of Sitting CMG Patient #25 showing normal uroflow, detrusor over activity, urgency incontinence, and normal pressure flow in a 62 year old female with a history of urgency frequency and urgency incontinence.

FIG. 10B—Upright Patient #25 (Example of Normal Uroflow, Detrusor over Activity, Urgency Incontinence, and Normal Pressure Flow)

A 62 year old female with a history of urgency frequency and urgency incontinence.

The standard urodynamic tracing indicates that Pdet is relatively quiet during the filling phase of the CMG. There is voluntary detrusor contraction which precedes voiding to 20 cm of H2O. The pressure flow curve is in the normal range.

NIRS indicates that throughout the filling, there is little change in the NIRS data, except that blood volume increases slightly prior to a small contraction in the detrusor, then decreases gradually as the bladder fills and the bladder wall thins. When the filling stops, blood volume increases slightly until voiding begins with voluntary contraction. We can see that blood volume increases again as the contraction is relaxed and continues to rise after the bladder is empty.

Non-Pathologic Cases

Figure 11A:
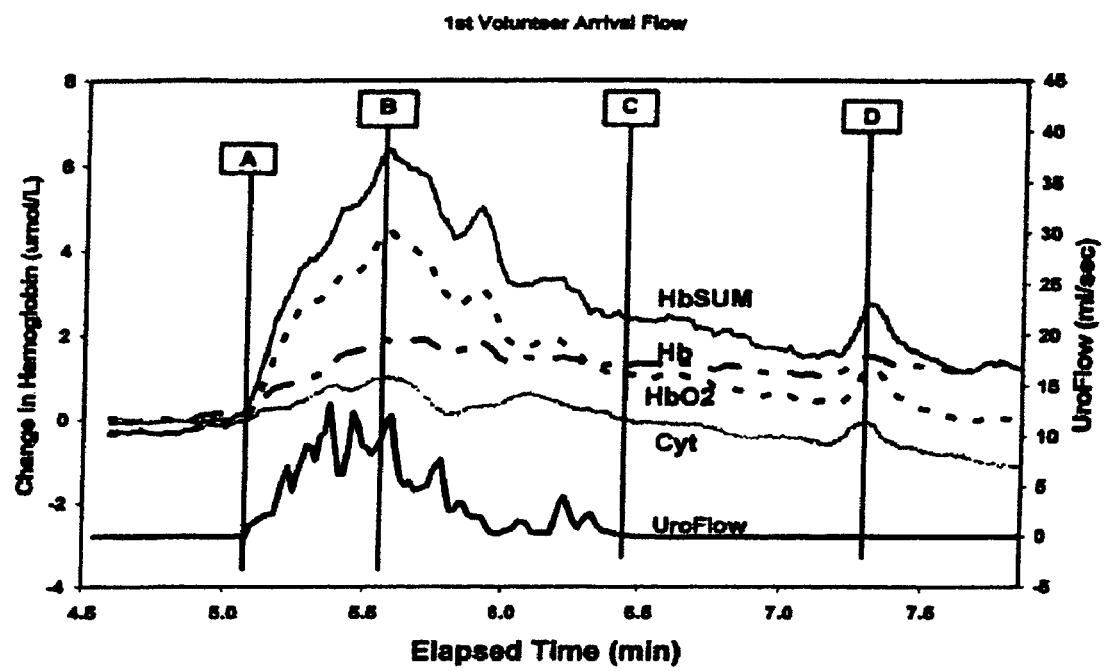
FIG. 11A is a urodynamic tracing of Uroflow $1^{st}$ Volunteer, $1^{st}$ showing normal bladder function in a 50 year old female in good health with no urologic complaints.

FIG. 11A—Uroflow $1^{st}$ Volunteer, $1^{st}$ Trial (Example of Normality)

A 50 year old female in good health with no urologic complaints.

The standard urodynamic tracing indicates normal uroflow with voiding of 370 cc and no residual volume.

NIRS indicates, from point A to point B, that there is an increase in blood volume with relaxation of the detrusor as urination is underway. Once peak flow occurs, midway between A and B there is a slight detrusor contraction to maintain the peak flow until point B, after which there is a prolonged gradually increasing detrusor contraction until voiding is complete at point C. This latter contraction is gentler than that used to sustain peak flow in that it is of the same magnitude but requires twice the duration to achieve that magnitude of change. A minute after voiding is complete there is brief relaxation impulse (point D).

Figure 11B:
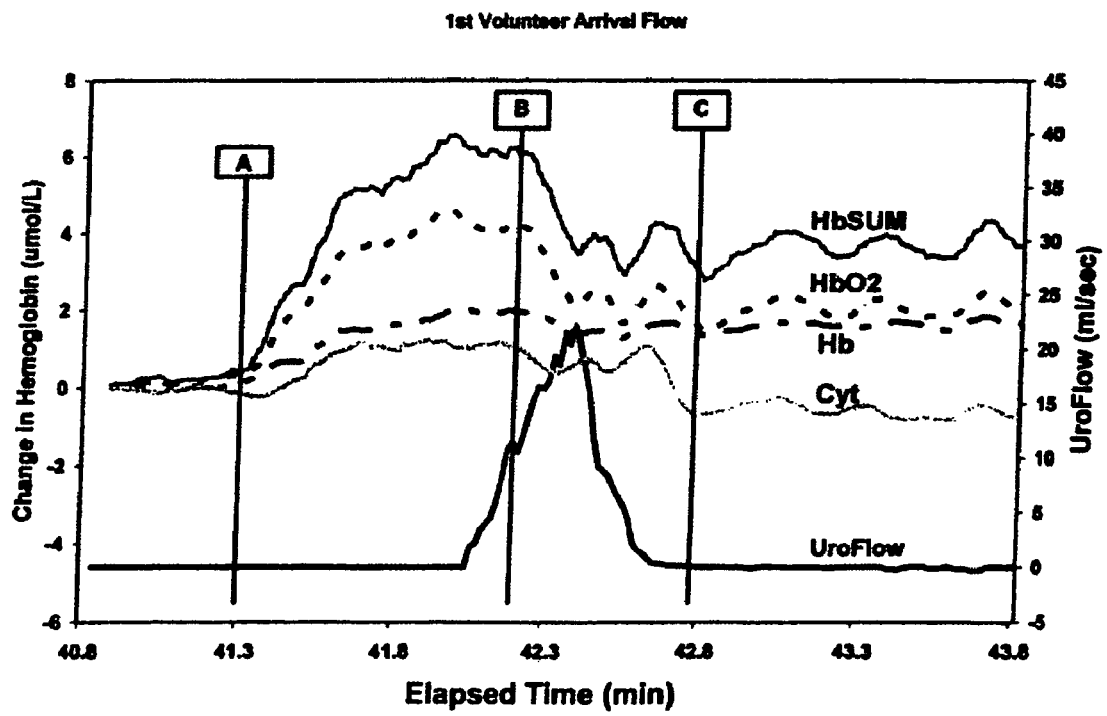
FIG. 11B is a urodynamic tracing of Uroflow $1^{st}$ Volunteer, $2^{nd}$ Trial showing normal bladder function in a 50 year old female in good health with no urologic complaints.

FIG. 11B—Uroflow $1^{st}$ Volunteer, $2^{nd}$ Trial (Example of Normality)

A 50 year old female in good health with no urologic complaints.

The standard urodynamic tracing indicates normal uroflow with voiding of 342 cc and no residual volume.

NIRS indicates that from point A to point B there is increasing blood volume in the detrusor, indicating relaxation of the detrusor and the sphincter in order to bring about passive urination without detrusor contraction. Just before point B, when urination begins, blood volume begins to decrease, indicating some contraction of the detrusor. After Point B, the contraction becomes stronger and urination reaches peak flow. There are several smaller contractions following this, as the subject felt empty, then contracted voluntarily again to confirm emptiness. The subsequent contractions are likely normal post-void rhythmic contractions.

Summary of Illustrative Implementation

In view of the above, one possible implementation of the methods described herein, according to an illustrative embodiment of the invention, may be described as follows.

Figure 12:
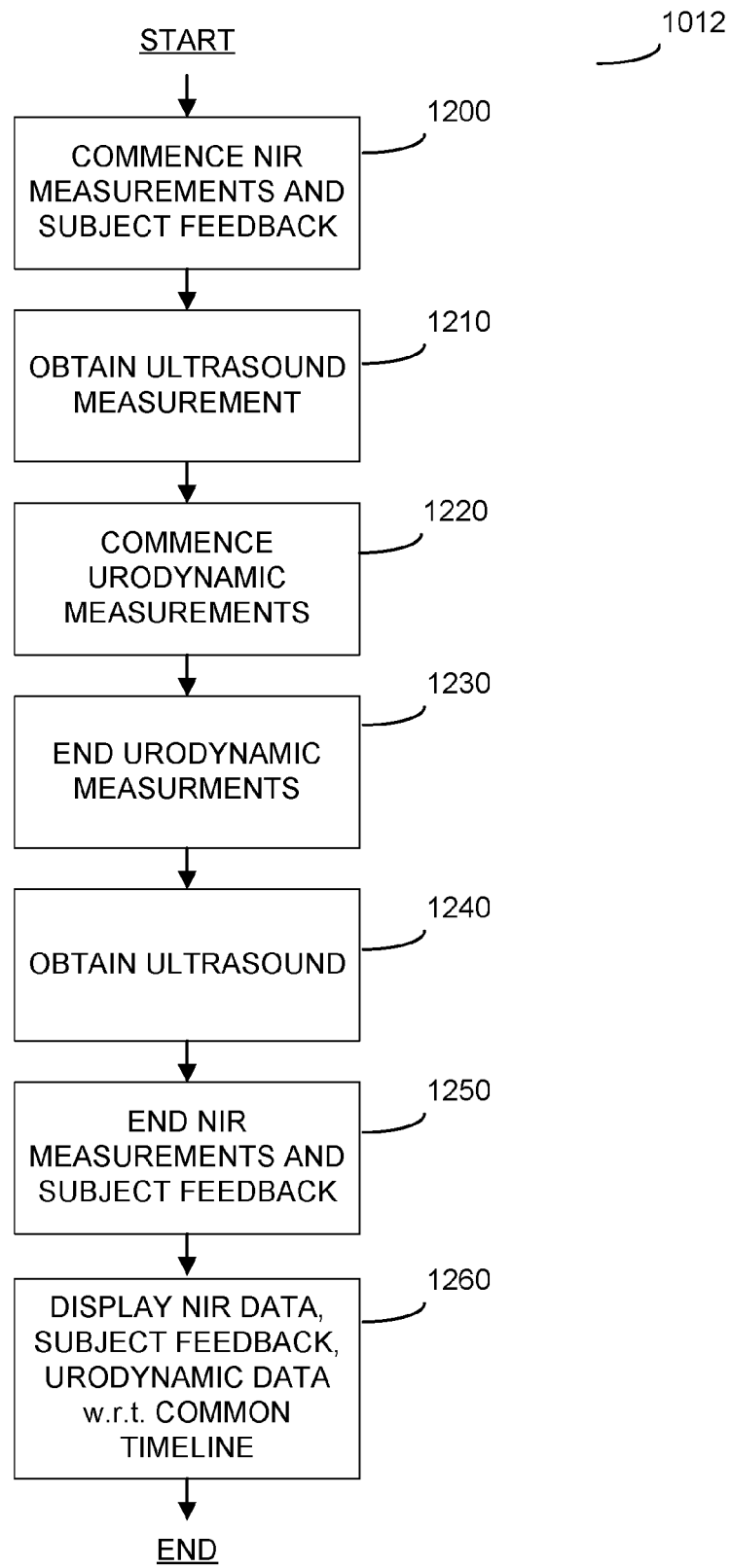
FIG. 12 is a flowchart of a bladder analysis routine according to an illustrative embodiment of the invention.

Referring to FIGS. 1 and 12, a bladder analysis routine according to an illustrative embodiment of the invention is shown generally at 1012.

In this embodiment, prior to execution of the bladder analysis routine 1012, the various input and measurement devices of the system 1000, including the user input devices 1040, the electromagnetic radiation measurement system 1020, the uroflow meter system 1050 and the ultrasound system 1060, are pre-configured by an operator of the system 1000. In particular, the operator positions the emitter and the detector of the electromagnetic radiation measurement system 1020 on the animal's skin adjacent to the animal's bladder. More particularly, in this embodiment this is achieved by ultrasonic positioning. More particularly still, in this embodiment the ultrasonic positioning includes transmitting ultrasonic energy from a transducer, and receiving reflected ultrasonic energy to determine the location of the animal's bladder. In this embodiment the animal is an adult human, and the detector is positioned on the human's skin at about 10 mm cephalic of the symphysis pubis. Also in this embodiment, the emitter and detector are positioned to have a separation of about 15-90 mm therebetween.

In this embodiment, such pre-configuration also includes shielding the emitter and the detector from ambient electromagnetic radiation. More particularly, in this embodiment this is achieved by installing a light shield, as described earlier herein and in FIGS. 1A-1C.

In the present embodiment, pre-configuration also includes selecting a suitable attenuator, which will be used to attenuate the electromagnetic radiation with which the bladder is irradiated. More particularly, in this embodiment attenuating includes filtering the electromagnetic radiation with which the bladder is irradiated. More particularly still, in this embodiment filtering includes filtering the electromagnetic radiation with a filter chamber having selectable variable density filters, operable to incrementally filter emitted electromagnetic radiation. Thus, in this embodiment, the pre-configuration of the system 1000 also includes pre-configuring a filter chamber, such as that described earlier herein and shown in FIGS. 2A-2C.

When the various input and measurement devices of the system 1000 have been pre-configured, in the present embodiment, execution of the bladder analysis routine 1012 by the processor circuit 1006 is commenced. Generally, it will be recalled that the bladder analysis routine 1012 programs or configures the processor circuit to receive signals from the detector of the measurement system 1020, the signals representing electromagnetic radiation detected from the bladder during irradiance of the bladder with electromagnetic radiation, and further directs the processor circuit to store data indicative of bladder function in response to the signals.

To achieve this, in this embodiment the bladder analysis routine 1012 includes a first block of codes 1200, which directs the processor circuit 1006 to signal the electromagnetic radiation measurement system 1020 to begin obtaining measurements of the bladder. In this embodiment the system 1020 includes the NIRO-300, which is directed to irradiate the bladder with its electromagnetic radiation emitter while detecting the electromagnetic radiation from the bladder with its detector. Thus, in the present embodiment, irradiating and detecting the bladder respectively include emitting and detecting near infrared (NIR), and wherein storing includes storing near infrared spectroscopy (NIRS) data. In this embodiment, irradiating the bladder includes emitting coherent electromagnetic radiation, which in this embodiment falls within a wavelength range of 750-950 nanometers. In this embodiment, the NIRO-300 is directed to receive signals representing near infrared (NIR) detected from the bladder during NIR irradiance of the bladder. In the present embodiment, block 1200 includes codes for directing the processor circuit 1006 to receive such signals from the NIRO-300 in real time, and to store the corresponding NIRS data in the bladder data store 1070. Alternatively, however, if desired, the NIRS data may be stored locally on the NIRO-300 until after all measurements have been completed, at which point the processor circuit 1006 may be directed to execute the NIRS routine 1022 to obtain the NIRS data from the NIRO-300 and store it in the bladder data store 1070. In this embodiment, the NIRS data received by the NIRO-300 corresponds to a first plurality of times during a first time period, which are recorded with the NIRS data. The NIRS data and corresponding times are stored by the processor circuit 1006 in the bladder data store 1070 (either in real time or subsequently, as discussed above).

Also in this embodiment, block 1.200 directs the processor circuit 1006 to begin receiving and storing subject feedback data for bladder sensation corresponding to an additional plurality of times during an additional time period. More particularly, in this embodiment the animal is a human subject, and the subject feedback data may be entered by either the subject or by an operator of the system 1000, using the user input devices 1040, such as a keyboard, mouse, or toggle switch, as described earlier herein. The processor circuit 1006 is directed to store such subject feedback data in the bladder data store 1070, along with the corresponding times.

In this embodiment, block 1210 directs the processor circuit 1006 to signal the ultrasound system 1060 to obtain ultrasonic measurements of bladder parameters of the animal, as described herein. Block 1210 directs the processor circuit 1006 to begin execute the ultrasound routine, to store these measurements in the bladder data store 1070.

Block 1220 then directs the processor circuit 1006 to signal the uroflow meter system 1050 to commence urodynamic measurements, as described earlier herein. Block 1220 also directs the processor circuit to begin executing the uroflow routine 1022, to cause the processor circuit to receive and store the resulting urodynamic measurements in the bladder data store 1070. Thus, in this embodiment, block 1220 directs the processor circuit to receive and store urodynamic data for the animal, the urodynamic data corresponding to a second plurality of times during a second time period. More particularly, in this embodiment the first and second pluralities of times (for the NIRS data and for the urodynamic data, respectively) are recorded with reference to a common timeline. In illustrative embodiments, the urodynamic data may include one or more of the following: bladder volume data; void volume data; uroflow data; filling cystometrogram data; and pressure flow data. More particularly, in this embodiment the urodynamic data includes uroflow data. As discussed earlier herein, it is advantageous for the NIRS measurements to commence prior to uroflow.

In this embodiment, such NIRS measurements, uroflow measurements and subject feedback inputs continue, from a time prior to commencement of uroflow, to a time following termination of uroflow. Thus, in this embodiment, irradiating and detecting include irradiating and detecting during bladder activity.

Following completion of bladder activity, blocks 1230, 1240 and 1250 direct the processor circuit 1006 to signal the uroflow meter system, the ultrasound system and the NIRO-300 to cease obtaining uroflow measurements, to obtain and store a further ultrasound measurement of bladder parameters in the bladder data store 1070, and to cease obtaining NIR and subject feedback data.

In this embodiment, as noted above, the bladder analysis routine 1012 includes codes for directing the processor circuit 1006 to receive the NIRS data from the NIRO-300 in real time, during the above measurement process. Alternatively, however, the NIRS data may be stored only on the NIRO-300 during the measurement process, in which case the NIRS routine 1022 may be executed by the processor circuit 1006 when the measurement process has been completed, to cause the processor circuit 1006 to receive signals representing the NIRS data from the NIRO-300, and to store the NIRS-data in the bladder data store 1070.

Thus, in the present embodiment, upon completion of the above measurement process, the bladder data store 1070 contains data representing NIRS measurements, uroflow measurements and ultrasound measurements of the bladder, as well as subject feedback data, each such piece of data accompanied by a corresponding time. The NIRS data, uroflow data and patient subject feedback data may be recorded for the same pluralities of times or for different pluralities of times, and the time periods during which these three types of data are obtained may be the same or different. In this embodiment, however, the time periods for the NIRS data, the uroflow data and the patient subject feedback data at least partly overlap. Moreover, in the present embodiment, the respective times for each of these three types of data are recorded with respect to a common timeline. As discussed earlier herein, the stored NIRS data is indicative of the animal's level of one or more of: oxygenated hemoglobin ($HbO_2$); de-oxygenated hemoglobin (Hb); oxidized cytochrome a, $a_3$; reduced cytochrome a, $a_3$; oxidized minus reduced forms of the cytochrome C oxidase (Cyt).

Following the above measurement and storage process, block 1260 directs the processor circuit 1006 to compare the NIRS data with one or more of the urodynamic data and subject feedback data in association with the common timeline. To achieve this, in this embodiment block 1260 directs the processor circuit to control a display monitor of the output devices 1030, to display a representation of the NIRS data. More particularly, in this embodiment the processor circuit is directed to control the display monitor to display a representation of the NIRS data with a representation of the urodynamic data and the subject feedback data in association with the common timeline. For example, block 1260 may direct the processor circuit 1006 to control the display monitor to generate a display such as that shown in FIG. 6B, which shows the NIRS data, the urodynamic data and the patient feedback data, all in relation to a common timeline. If desired, block 1260 may also direct the processor circuit 1006 to store representations of these types of data in electronic form in the storage device 1004, or to output them onto other media such as paper printouts, CD-ROMs or diskettes using others of the output devices 1030.

The bladder analysis routine is then ended.

Although the foregoing describes an illustrative embodiment in which the various forms of data are obtained and coordinated through the execution of a bladder analysis routine, alternatively, NIRS measurements, urodynamic measurements, and subject feedback data may be obtained and stored independently, with reference to a common timeline. In such embodiments, an alternative bladder analysis routine may synthesize the different forms of measurement data, to produce displays or other outputs such as that shown in FIG. 6B.

While specific embodiments of the invention have been described and illustrated, such embodiments should be considered illustrative of the invention only and not as limiting the invention as construed in accordance with the accompanying claims.

What is claimed is:

1. A method for monitoring bladder function in an animal having a bladder, the method comprising:
    positioning an electromagnetic radiation emitter and an electromagnetic radiation detector on a skin surface of the animal adjacent to the animal's bladder;
    emitting near infrared electromagnetic radiation (NIR) at the bladder with the electromagnetic radiation emitter while detecting the NIR with the electromagnetic radiation detector;
    collecting near infrared spectroscopy (NIRS) data representative of the detected NIR prior to, during, and following bladder filling and voiding;
    correlating the detected NIRS data to changes in oxygenation and hemodynamic parameters prior to, during, and following bladder filling and voiding to provide an indication of bladder function; and
    storing the collected NIRS data for the animal, wherein the NIRS data corresponds to a first plurality of times during a first time period.

2. The method of claim 1, wherein emitting comprises emitting coherent NIR.

3. The method of claim 1, wherein positioning comprises ultrasonic positioning.

4. The method of claim 3, wherein ultrasonic positioning comprises:
    (a) transmitting ultrasonic energy from a transducer; and
    (b) receiving reflected ultrasonic energy to determine the location of the animal's bladder.

5. The method of claim 1, wherein positioning the detector on the animal's skin comprises positioning the detector about 10 mm cephalic of the symphysis pubis of an adult human.

6. The method of claim 1, wherein emitting NIR comprises emitting electromagnetic radiation within a wavelength range of 750-950 nanometers.

7. The method of claim 1, further comprising shielding the emitter and the detector from ambient electromagnetic radiation.

8. The method of claim 1, further comprising attenuating the electromagnetic radiation with which the bladder is irradiated.

9. The method of claim 8, wherein attenuating comprises filtering the electromagnetic radiation with which the bladder is irradiated.

10. The method of claim 9, wherein filtering comprises filtering the electromagnetic radiation with a filter chamber having selectable variable density filters, operable to incrementally filter emitted electromagnetic radiation.

11. The method of claim 1, further comprising obtaining ultrasonic measurements of bladder parameters of the animal.

12. The method of claim 1, wherein positioning comprises positioning the emitter and the detector to have a separation of about 15-90 mm therebetween.

13. The method of claim 1, further comprising receiving and storing urodynamic data for the animal, the urodynamic data corresponding to a second plurality of times during a second time period wherein said first and second pluralities of times are recorded with reference to a common timeline.

14. The method of claim 13, further comprising receiving and storing subject feedback data for bladder sensation corresponding to an additional plurality of times during an additional time period, wherein the animal is a human subject.

15. The method of claim 14, further comprising comparing said NIRS data with one or more of said urodynamic data and subject feedback data in association with the common timeline.

16. The method of claim 14, further comprising displaying said NIRS data with one or more of said urodynamic data and subject feedback data in association with the common timeline.

17. The method of claim 13, further comprising comparing said NIRS data with said urodynamic data in association with the common timeline.

18. The method of claim 13, further comprising displaying a representation of said NIRS data with a representation of said urodynamic data in association with the common timeline.

19. The method of claim 13, wherein the urodynamic data comprises one or more of the following: bladder volume data; void volume data; uroflow data; filling cystometrogram data; and pressure flow data.

20. The method of claim 13, wherein the first plurality of times is different from the second plurality of times.

21. The method of claim 13, wherein the first plurality of times is the same as the second plurality of times.

22. The method of claim 13, wherein said first time period at least partly overlaps with said second time period.

23. The method of claim 1, further comprising receiving and storing subject feedback data for bladder sensation corresponding to an additional plurality of times during an additional time period, wherein the animal is a human subject.

24. The method of claim 23, wherein said first plurality of times is different from said additional plurality of times.

25. The method of claim 23, wherein said first plurality of times is the same as said additional plurality of times.

26. The method of claim 23, wherein said first time period at least partly overlaps with said additional time period.

27. The method of claim 1, further comprising displaying a representation of said NIRS data.

28. The method of claim 1, wherein said NIRS data is indicative of the animal's level of one or more of oxygenated hemoglobin (Hb02); de-oxygenated hemoglobin (Hb); oxidized cytochrome a, $a_3$; reduced cytochrome a, $a_3$; and oxidized minus reduced forms of the cytochrome C oxidase (Cyt).

* * * * *